(12) United States Patent
Libbus

(10) Patent No.: US 11,724,109 B2
(45) Date of Patent: Aug. 15, 2023

(54) SYSTEM AND METHOD FOR SUSTAINED BAROREFLEX STIMULATION

(71) Applicant: Cardiac Pacemakers, Inc., St. Paul, MN (US)

(72) Inventor: Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 331 days.

(21) Appl. No.: 16/733,780

(22) Filed: Jan. 3, 2020

(65) Prior Publication Data

US 2020/0139128 A1     May 7, 2020

Related U.S. Application Data

(63) Continuation of application No. 15/465,425, filed on Mar. 21, 2017, now abandoned, which is a continuation of application No. 13/459,669, filed on Apr. 30, 2012, now abandoned, which is a continuation of application No. 10/962,845, filed on Oct. 12, 2004, now Pat. No. 8,175,705.

(51) Int. Cl.
    *A61N 1/36*     (2006.01)

(52) U.S. Cl.
    CPC .............................. *A61N 1/36114* (2013.01)

(58) Field of Classification Search
    CPC ............ A61N 1/36564; A61N 1/36135; A61N 1/3606; A61N 1/37; A61N 1/36139; A61N 1/0551; A61N 1/36057; A61N 1/36128; A61B 5/4035; A61B 2018/00434
See application file for complete search history.

(56) References Cited

U.S. PATENT DOCUMENTS

| | | |
|---|---|---|
| 3,421,511 A | 1/1969 | Schwartz et al. |
| 3,650,277 A | 3/1972 | Sjostrand et al. |
| 4,541,432 A | 9/1985 | Molina-Negro et al. |

(Continued)

FOREIGN PATENT DOCUMENTS

| | | |
|---|---|---|
| EP | 1421973 A3 | 5/2004 |
| EP | 1426078 A1 | 6/2004 |

(Continued)

OTHER PUBLICATIONS

"U.S. Appl. No. 10/962,845, Appeal Brief mailed Sep. 26, 2007", 33 pgs.

(Continued)

*Primary Examiner* — Deborah L Malamud
(74) *Attorney, Agent, or Firm* — Schwegman Lundberg & Woessner, P.A.

(57) ABSTRACT

Various aspects of the present subject matter provide an implantable medical device. In various embodiments, the device comprises a baroreflex stimulator and a controller. The baroreflex stimulator is adapted to generate a stimulation signal to stimulate a baroreflex. The controller is adapted to communicate with the baroreflex stimulator and implement a baroreflex stimulation protocol to vary an intensity of the baroreflex stimulation provided by the stimulation signal to abate baroreflex adaptation. According to various embodiments, the controller is adapted to implement the baroreflex stimulation protocol to periodically modulate the baroreflex stimulation to produce an effect that mimics an effect of pulsatile pressure. Other aspects are provided herein.

20 Claims, 15 Drawing Sheets

(56) References Cited

U.S. PATENT DOCUMENTS

| | | |
|---|---|---|
| 4,759,368 A | 7/1988 | Spanton et al. |
| 4,763,646 A | 8/1988 | Lekholm |
| 4,791,931 A | 12/1988 | Slate |
| 4,938,223 A | 7/1990 | Charters et al. |
| 5,111,815 A | 5/1992 | Mower |
| 5,190,035 A | 3/1993 | Salo et al. |
| 5,199,428 A | 4/1993 | Obel et al. |
| 5,203,326 A | 4/1993 | Collins |
| 5,243,980 A | 9/1993 | Mehra |
| 5,318,592 A | 6/1994 | Schaldach |
| 5,330,507 A | 7/1994 | Schwartz |
| 5,356,425 A | 10/1994 | Bardy et al. |
| 5,403,351 A | 4/1995 | Saksena |
| 5,411,531 A | 5/1995 | Hill et al. |
| 5,437,285 A | 8/1995 | Verrier et al. |
| 5,507,784 A | 4/1996 | Hill et al. |
| 5,522,854 A | 6/1996 | Ideker et al. |
| 5,578,061 A | 11/1996 | Stroetmann et al. |
| 5,658,318 A | 8/1997 | Stroetmann et al. |
| 5,690,681 A | 11/1997 | Geddes et al. |
| 5,700,282 A | 12/1997 | Zabara |
| 5,731,848 A | 3/1998 | Patel et al. |
| 5,916,239 A | 6/1999 | Geddes et al. |
| 5,928,272 A | 7/1999 | Adkins et al. |
| 6,006,134 A | 12/1999 | Hill et al. |
| 6,058,331 A | 5/2000 | King |
| 6,073,048 A | 6/2000 | Kieval et al. |
| 6,134,470 A | 10/2000 | Hartlaub |
| 6,161,042 A | 12/2000 | Hartley et al. |
| 6,178,349 B1 | 1/2001 | Kieval |
| 6,181,966 B1 | 1/2001 | Nigam |
| 6,240,314 B1 | 5/2001 | Plicchi et al. |
| 6,272,377 B1 | 8/2001 | Sweeney et al. |
| 6,285,909 B1 | 9/2001 | Sweeney et al. |
| 6,292,695 B1 | 9/2001 | Webster, Jr. et al. |
| 6,330,477 B1 | 12/2001 | Casavant |
| 6,371,922 B1 | 4/2002 | Baumann et al. |
| 6,400,982 B2 | 6/2002 | Sweeney et al. |
| 6,415,183 B1 | 7/2002 | Scheiner et al. |
| 6,421,557 B1 | 7/2002 | Meyer |
| 6,449,507 B1 | 9/2002 | Hill et al. |
| 6,473,644 B1 | 10/2002 | Terry, Jr. et al. |
| 6,487,450 B1 | 11/2002 | Chen et al. |
| 6,493,585 B2 | 12/2002 | Plicchi et al. |
| 6,493,586 B1 | 12/2002 | Stahmann et al. |
| 6,511,500 B1 | 1/2003 | Rahme |
| 6,512,949 B1 | 1/2003 | Combs et al. |
| 6,522,926 B1 | 2/2003 | Kieval et al. |
| 6,532,388 B1 | 3/2003 | Hill et al. |
| 6,542,774 B2 | 4/2003 | Hill et al. |
| 6,564,096 B2 | 5/2003 | Mest |
| 6,611,713 B2 | 8/2003 | Schauerte |
| 6,622,041 B2 | 9/2003 | Terry, Jr. et al. |
| 6,622,048 B1 | 9/2003 | Mann et al. |
| 6,628,987 B1 | 9/2003 | Hill et al. |
| 6,631,290 B1 | 10/2003 | Guck et al. |
| 6,711,442 B1 | 3/2004 | Swerdlow et al. |
| 6,850,801 B2 | 2/2005 | Kieval et al. |
| 6,985,774 B2 | 1/2006 | Kieval et al. |
| 7,096,064 B2 | 8/2006 | Deno et al. |
| 7,123,961 B1 | 10/2006 | Kroll et al. |
| 7,123,967 B2 | 10/2006 | Weinberg |
| 7,158,832 B2 | 1/2007 | Kieval et al. |
| 7,221,979 B2 | 5/2007 | Zhou et al. |
| 7,260,431 B2 | 8/2007 | Libbus et al. |
| 7,299,086 B2 | 11/2007 | McCabe et al. |
| 7,542,800 B2 | 6/2009 | Libbus et al. |
| 7,551,958 B2 | 6/2009 | Libbus et al. |
| 7,570,999 B2 | 8/2009 | Libbus et al. |
| 7,587,238 B2 | 9/2009 | Moffitt et al. |
| 7,623,926 B2 | 11/2009 | Rossing et al. |
| 7,657,312 B2 | 2/2010 | Pastore et al. |
| 7,660,628 B2 | 2/2010 | Libbus et al. |
| 7,769,450 B2 | 8/2010 | Libbus et al. |
| 7,783,353 B2 | 8/2010 | Libbus et al. |
| 7,801,601 B2 | 9/2010 | Maschino et al. |
| 7,831,305 B2 | 11/2010 | Gliner |
| 7,840,271 B2 | 11/2010 | Kieval |
| 7,873,413 B2 | 1/2011 | McCabe et al. |
| 8,000,793 B2 | 8/2011 | Libbus |
| 8,126,559 B2 | 2/2012 | Libbus |
| 8,126,560 B2 | 2/2012 | Scheiner et al. |
| 8,175,705 B2 | 5/2012 | Libbus |
| 8,285,389 B2 | 10/2012 | Libbus et al. |
| 8,452,398 B2 | 5/2013 | Libbus et al. |
| 8,457,746 B2 | 6/2013 | Libbus |
| 8,626,301 B2 | 1/2014 | Libbus |
| 9,031,650 B2 | 5/2015 | McCabe et al. |
| 9,211,412 B2 | 12/2015 | McCabe et al. |
| 9,265,648 B2 | 2/2016 | Chang et al. |
| 9,265,948 B2 | 2/2016 | Libbus et al. |
| 9,561,373 B2 | 2/2017 | Libbus et al. |
| 9,950,170 B2 | 4/2018 | Libbus et al. |
| 9,962,548 B2 | 5/2018 | McCabe et al. |
| 10,369,367 B2 | 8/2019 | Libbus et al. |
| 2002/0026221 A1 | 2/2002 | Hill et al. |
| 2002/0026222 A1 | 2/2002 | Schauerte et al. |
| 2002/0058877 A1 | 5/2002 | Baumann et al. |
| 2002/0065473 A1 | 5/2002 | Wang et al. |
| 2002/0068875 A1 | 6/2002 | Schroeppel et al. |
| 2002/0072770 A1 | 6/2002 | Pless |
| 2002/0107553 A1 | 8/2002 | Hill et al. |
| 2002/0120304 A1 | 8/2002 | Mest |
| 2002/0123769 A1 | 9/2002 | Panken et al. |
| 2002/0123770 A1 | 9/2002 | Combs et al. |
| 2002/0143369 A1 | 10/2002 | Hill et al. |
| 2002/0165586 A1 | 11/2002 | Hill et al. |
| 2003/0003052 A1 | 1/2003 | Hampton |
| 2003/0004549 A1 | 1/2003 | Hill et al. |
| 2003/0040774 A1 | 2/2003 | Terry, Jr. et al. |
| 2003/0045909 A1 | 3/2003 | Gross et al. |
| 2003/0060848 A1 | 3/2003 | Keival et al. |
| 2003/0060857 A1 | 3/2003 | Perrson et al. |
| 2003/0060858 A1 | 3/2003 | Kieval et al. |
| 2003/0078623 A1 | 4/2003 | Weinberg et al. |
| 2003/0078629 A1 | 4/2003 | Chen |
| 2003/0100924 A1 | 5/2003 | Foreman et al. |
| 2003/0149450 A1 | 8/2003 | Mayberg |
| 2003/0195571 A1 | 10/2003 | Burnes et al. |
| 2003/0199936 A1 | 10/2003 | Struble et al. |
| 2003/0212440 A1 | 11/2003 | Boveja |
| 2003/0229380 A1 | 12/2003 | Adams et al. |
| 2004/0049120 A1 | 3/2004 | Cao et al. |
| 2004/0068299 A1 | 4/2004 | Laske et al. |
| 2004/0088009 A1 | 5/2004 | Degroot |
| 2004/0127792 A1 | 7/2004 | Siejko et al. |
| 2004/0138518 A1 | 7/2004 | Rise et al. |
| 2004/0138719 A1 | 7/2004 | Cho et al. |
| 2004/0193231 A1 | 9/2004 | David et al. |
| 2004/0254616 A1 | 12/2004 | Rossing et al. |
| 2005/0027320 A1 | 2/2005 | Nehls et al. |
| 2005/0055060 A1 | 3/2005 | Koh et al. |
| 2005/0096705 A1 | 5/2005 | Pastore et al. |
| 2005/0143779 A1 | 6/2005 | Libbus |
| 2005/0143785 A1 | 6/2005 | Libbus |
| 2005/0148896 A1 | 7/2005 | Siejko et al. |
| 2005/0149126 A1 | 7/2005 | Libbus |
| 2005/0149127 A1 | 7/2005 | Libbus |
| 2005/0149128 A1 | 7/2005 | Heil, Jr. et al. |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149155 A1 | 7/2005 | Scheiner et al. |
| 2005/0149156 A1 | 7/2005 | Libbus et al. |
| 2005/0197674 A1 | 9/2005 | McCabe et al. |
| 2005/0261741 A1 | 11/2005 | Libbus et al. |
| 2006/0004417 A1 | 1/2006 | Rossing et al. |
| 2006/0079945 A1 | 4/2006 | Libbus |
| 2006/0106429 A1 | 5/2006 | Libbus et al. |
| 2006/0116737 A1 | 6/2006 | Libbus |
| 2006/0122675 A1 | 6/2006 | Libbus et al. |

(56) References Cited

U.S. PATENT DOCUMENTS

| | | | |
|---|---|---|---|
| 2006/0206154 | A1 | 9/2006 | Moffitt et al. |
| 2006/0217772 | A1 | 9/2006 | Libbus et al. |
| 2006/0224188 | A1 | 10/2006 | Libbus et al. |
| 2006/0241725 | A1 | 10/2006 | Libbus |
| 2006/0271108 | A1 | 11/2006 | Libbus et al. |
| 2007/0021799 | A1 | 1/2007 | Kieval et al. |
| 2007/0142864 | A1 | 6/2007 | Libbus et al. |
| 2007/0185543 | A1 | 8/2007 | Rossing et al. |
| 2008/0167693 | A1 | 7/2008 | Kieval et al. |
| 2008/0228238 | A1 | 9/2008 | Libbus |
| 2009/0018596 | A1 | 1/2009 | Kieval |
| 2009/0228060 | A1 | 9/2009 | Libbus et al. |
| 2010/0023090 | A1 | 1/2010 | Jaax et al. |
| 2010/0121399 | A1 | 5/2010 | McCabe et al. |
| 2010/0286740 | A1 | 11/2010 | Libbus et al. |
| 2011/0082514 | A1 | 4/2011 | Libbus et al. |
| 2011/0106199 | A1 | 5/2011 | Mccabe et al. |
| 2011/0295333 | A1 | 12/2011 | Libbus |
| 2012/0215279 | A1 | 8/2012 | Libbus |
| 2013/0253616 | A1 | 9/2013 | Libbus et al. |
| 2015/0032188 | A1 | 1/2015 | Libbus et al. |
| 2015/0238766 | A1 | 8/2015 | Mccabe et al. |
| 2016/0082259 | A1 | 3/2016 | Mccabe et al. |
| 2016/0129247 | A1 | 5/2016 | Lee et al. |
| 2016/0228711 | A1 | 8/2016 | Libbus et al. |
| 2016/0279422 | A1 | 9/2016 | Libbus et al. |
| 2017/0189682 | A1 | 7/2017 | Libbus |
| 2018/0289966 | A1 | 10/2018 | Libbus et al. |

FOREIGN PATENT DOCUMENTS

| | | |
|---|---|---|
| EP | 1871464 B1 | 3/2017 |
| EP | 1804901 B1 | 5/2018 |
| JP | 6246010 A | 9/1994 |
| JP | 11500930 A | 1/1999 |
| JP | 2001198228 A | 7/2001 |
| JP | 2002513656 A | 5/2002 |
| JP | 2002514478 A | 5/2002 |
| JP | 2004-523265 A | 8/2004 |
| JP | 2004523265 A | 8/2004 |
| JP | 2004526471 A | 9/2004 |
| JP | 2005501617 A | 1/2005 |
| JP | 2007500551 A1 | 1/2007 |
| WO | WO-9625978 A1 | 8/1996 |
| WO | WO-9956822 A1 | 11/1999 |
| WO | WO-9958191 A1 | 11/1999 |
| WO | WO-2002026314 A1 | 4/2002 |
| WO | WO-0247761 A2 | 6/2002 |
| WO | WO-03018108 A3 | 3/2003 |
| WO | WO-03020364 A2 | 3/2003 |
| WO | WO-03076008 A1 | 9/2003 |
| WO | WO-2003076008 A1 | 9/2003 |
| WO | WO-03099377 A1 | 12/2003 |
| WO | WO-2005000396 A1 | 1/2005 |
| WO | WO-2005011803 A2 | 2/2005 |
| WO | WO-2006031331 A1 | 3/2006 |
| WO | WO-2006044025 A1 | 4/2006 |
| WO | WO-2006107675 A1 | 10/2006 |
| WO | WO-2008063396 A1 | 5/2008 |
| WO | WO-2008144354 A1 | 11/2008 |
| WO | WO-2011088222 A1 | 7/2011 |

OTHER PUBLICATIONS

"U.S. Appl. No. 10/962,845, Final Office Action dated Jan. 26, 2007", 7 pgs.
"U.S. Appl. No. 10/962,845, Non Final Office Action dated Apr. 7, 2011", 14 pgs.
"U.S. Appl. No. 10/962,845, Non Final Office Action dated May 12, 2006", 10 pgs.
"U.S. Appl. No. 10/962,845, Notice of Allowance dated Jan. 13, 2012", 7 pgs.
"U.S. Appl. No. 10/962,845, Notice of Allowance dated Sep. 22, 2011", 7 pgs.
"U.S. Appl. No. 10/962,845, Preliminary Amendment filed Apr. 25, 2005", 11 pgs.
"U.S. Appl. No. 10/962,845, Response filed Oct. 12, 2006 to Non Final Office Action dated May 12, 2006", 14 pgs.
"U.S. Appl. No. 10/962,845, Response filed Aug. 8, 2011 to Non Final Office Action dated Apr. 7, 2011", 14 pgs.
"U.S. Appl. No. 13/459,669, Advisory Action dated Jun. 27, 2014", 3 pgs.
"U.S. Appl. No. 13/459,669, Appeal Brief filed Sep. 15, 2014", 22 pgs.
"U.S. Appl. No. 13/459,669, Appeal Decision mailed Jan. 23, 2017", 7 pgs.
"U.S. Appl. No. 13/459,669, Final Office Action dated Mar. 20, 2014", 9 pgs.
"U.S. Appl. No. 13/459,669, Non Final Office Action dated Nov. 20, 2013", 9 pgs.
"U.S. Appl. No. 13/459,669, Response filed Feb. 12, 2014 to Non Final Office Action dated Nov. 20, 2014", 11 pgs.
"U.S. Appl. No. 13/459,669, Response filed Jun. 18, 2014 to Final Office Action dated Mar. 20, 2014", 13 pgs.
"U.S. Appl. No. 13/459,669, Response filed Oct. 10, 2013 to Restriction Requirement dated Sep. 12, 2013", 7 pgs.
"U.S. Appl. No. 13/459,669, Restriction Requirement dated Sep. 12, 2013", 6 pgs.
"U.S. Appl. No. 15/465,425, Advisory Action dated May 20, 2019", 3 pgs.
"U.S. Appl. No. 15/465,425, Final Office Action dated Mar. 8, 2019", 7 pgs.
"U.S. Appl. No. 15/465,425, Non Final Office Action dated Sep. 12, 2018", 6 pgs.
"U.S. Appl. No. 15/465,425, Pre-Appeal Brief filed Sep. 4, 2019", 5 pgs.
"U.S. Appl. No. 15/465,425, Preliminary Amendment filed Apr. 5, 2017", 6 pgs.
"U.S. Appl. No. 15/465,425, Resonse filed Dec. 12, 2018 to Non Final Office Action dated Sep. 12, 2018", 9 pgs.
"U.S. Appl. No. 15/465,425, Response filed Jul. 24, 2018 to Restriction Requirement dated May 30, 2018", 7 pgs.
"U.S. Appl. No. 15/465,425, Response filed Apr. 29, 2019 to Final Office Action dated Mar. 8, 2019", 9 pgs.
"U.S. Appl. No. 15/465,425, Restriction Requirement dated May 30, 2018", 7 pgs.
"European Application Serial No. 05789106.1, Communication Pursuant to Article 94(3) EPC dated Feb. 7, 2017", 3 pgs.
"European Application Serial No. 05789106.1, Response filed Jun. 20, 2017 to Communication Pursuant to Article 94(3) EPC dated Feb. 7, 2017", 18 pgs.
"International Search Report and Written Opinion for Application No. PCT/US2005/029540, dated Jan. 18, 2006", 12 Pages.
"Japanese Application Serial No. 2007-536687, Examiners Decision of Final Refusal dated Jan. 21, 2013", With English Translation, 5 pgs.
"Japanese Application Serial No. 2007-536687, Office Action dated May 2, 2011", With English Translation, 7 Pgs.
"Japanese Application Serial No. 2007-536687, Office Action dated Jun. 19, 2012", With English Translation, 9 pgs.
"Japanese Application Serial No. 2007-536687, Office Action dated Nov. 25, 2011", (w/ English Translation), 9 pgs.
"Japanese Application Serial No. 2007-536687, Response filed Apr. 13, 2012 to Office Action dated Nov. 25, 2011", English Claims with response, 14 pgs.
"Japanese Application Serial No. 2007-536687, Response filed Aug. 2, 2011 to Office Action dated May 2, 2011", (w/ English Translation of Amended Claims), 17 pgs.
Andersen, H, et al., "Long-term follow-up of patients from a randomised trial of atrial versus ventricular pacing forsick-sinus syndrome", Lancet, 350(9086), (Oct. 25, 1997), 1210-6.
Benchimol, A, et al., "Cardiac hemodynamics during stimulation of the right atrium, right ventricle, and left ventricle in normal and abnormal hearts", Circulation, 33(6), (Jun. 1966), 933-44.

(56) References Cited

OTHER PUBLICATIONS

Bevan, J A, et al., "Postganglionic sympathetic delay in vascular smooth muscle", Journal of Pharmacology & Experimental Therapeutics, 152(2), (May 1966), 221-30.
Bevan, J A, et al., "Sympathetic nerve-free vascular muscle", Journal of Pharmacology & Experimental Therapeutics, 157(1), (Jul. 1967), 117-24.
Bilgutay, A M, et al., "A new concept in the treatment of hypertension utilizing an implantable electronic device: "Baropacer"", Trans Am Soc Artif Intern Organs., 10, (1964), 387-395.
Bilgutay, A M, et al., "Vagal tuning for the control of supraventricular arrhythmias", Surgical Forum, 16, (1965), 151-3.
Bilgutay, A. M, et al., "Vagal tuning. A new concept in the treatment of supraventricular arrhythmias, angina pectoris, and heart failure", Journal of Thoracic and Cardiovascular Surgery, 56(1), (Jul. 1968), 71-82.
Borst, C, et al., "Optimal frequency of carotid sinus nerve stimulation in treatment of angina pectoris", Cardiovascular Research, 8(5), (Sep. 1974), 674-80.
Braunwald, E, et al., "Carotid sinus nerve stimulation in the treatment of angina pectoris and supraventricular tachycardia", California Medicine, 112(3), (Mar. 1970), 41-50.
Braunwald, E, et al., "Relief of angina pectoris by electrical stimulation of the carotid-sinus nerves", New England Journal of Medicine, 277(24), (Dec. 14, 1967), 1278-83.
Chapleau, M. W., et al., "Contrasting effects of static and pulsatile pressure on carotid baroreceptor activity in dogs", Circulation, vol. 61, No. 5, (Nov. 1987), 648-658.
Chapleau, Mark W., "Pulsatile activation of baroreceptors causes central facilitation of baroreflex", American Journal Physiol Heart Circ Physiol, (Jun. 1989), 256: H1735-1741.
Coleridge, J C, et al., "Relationship between pulmonary arterial pressure and impulse activity in pulmonary arterial baroreceptor fibres", Journal of Physiology, 158, (Sep. 1961), 197-205.
Coleridge, J C, et al., "The distribution, connexions and histology of baroreceptors in the pulmonary artery, with some observations on the sensory innervation of the ductus arteriosus", Journal of Physiology, 156, (May 1961), 591-602.
Cooper, Terry B, et al., "Neural effects on sinus rate and atrioventricular conduction produced by electrical stimulation from a transvenous electrode catheter in the canine right pulmonary artery", Circulation Research, vol. 46, No. 1, (Jan. 1980), 48-57.
Courtice, G P, et al., "Effect of frequency and impulse pattern on the non-cholinergic cardiac response to vagal stimulation in the toad, Bufo marinus", Journal of the Autonomic Nervous System, 48(3), (Aug. 1994), 267-72.
Dart, Jr., C H, et al., "Carotid sinus nerve stimulation treatment of angina refractory to other surgical procedures", Annals of Thoracic Surgery, 11(4), (Apr. 1971), 348-59.
De Landsheere, D, et al., "Effect of spinal cord stimulation on regional myocardial perfusion assessed by positron emission tomography", American Journal of Cardiology, 69(14), (May 1, 1992), 1143-9.
Dunning, A. J., "Electrostimulation of the Carotid Sinus Nerve in Angina Pectoris", University Department of Medicine, Binnengasthuis, Amsterdam; Printed by Royal VanGorcum, Assen, Netherlands, (1971), 1-92.
Epstein, S. E., et al., "Treatment of angina pectoris by electrical stimulation of the carotid-sinus nerves", New England Journal of Medicine, 280(18), (May 1, 1969), 971-978.
Farrehi, C, "Stimulation of the carotid sinus nerve in treatment of angina pectoris", American Heart Journal, 80(6), (Dec. 1970), 759-65.
Feliciano, L, et al., "Vagal nerve stimulation releases vasoactive intestinal peptide which significantly increases coronary artery blood flow", Cardiovascular Research, 40(1), (Oct. 1998), 45-55.
Fromer, M, et al., "Ultrarapid subthreshold stimulation for termination of atrioventricular node reentrant tachycardia", Journal of the American College of Cardiology, 20(4), (Oct. 1992), 879-83.

Grassi, Guido, et al., "Baroreflex and non-baroreflex modulation of vagal cardiac control after myocardial infarction", Am J Cardiol., 84(5), (Sep. 1, 1999), 525-529.
Griffith, Lawrence S.C., et al., "Electrical Stimulation of the Carotid Sinus Nerve in Normotensive and Renal Hypertensive Dogs", Circulation, 28, (Jul.-Dec. 1963), 730.
Heil, Jr., Ronald W., et al., "Barorelflex Stimulation System to Reduce Hypertension", U.S. Appl. No. 10/746,134, filed Dec. 24, 2003, 78 pgs.
Henning, R J, et al., "Effects of autonomic nerve stimulation, asynchrony, and load on dP/dtmax and on dP/dtmin", American Journal of Physiology, 260(4 Pt 2), (Apr. 1991), H1290-H1298.
Henning, R J, et al., "Vagal nerve stimulation increases right ventricular contraction and relaxation and heart rate", Cardiovascular Research, 32(5), (Nov. 1996), 846-53.
Henning, R J, et al., "Vagal stimulation attenuates sympathetic enhancement of left ventricular function", American Journal of Physiology, 258(5 Pt 2), (May 1990), H1470-5.
Hood Jr., W B, et al., "Asynchronous contraction due to late systolic bulging at left ventricular pacing sites", American Journal of Physiology, 217(1), (Jul. 1969), 215-21.
Ishise, H, et al., "Time course of sympathovagal imbalance and left ventricular dysfunction in conscious dogs with heart failure", Journal of Applied Physiology, 84(4), (Apr. 1998), 1234-41.
Jessurun, G A, et al., "Coronary blood flow dynamics during transcutaneous electrical nerve stimulation for stable angina pectoris associated with severe narrowing of one major coronary artery", American Journal of Cardiology, 82(8), erratum appears in Am J Cardiol Feb. 15, 1999;83(4):642, (Oct. 15, 1998), 921-6.
Kandel, Eric R, et al., "Part VII: Arousal, Emotion, and Behavioral Homeostasis", in: Principles of Neural Science, New York : McGraw-Hill, Health Professions Division, (2000), 966-969.
Karpawich, P P, et al., "Altered cardiac histology following apical right ventricular pacing in patients with congenital atrioventricular block", Pacing Clin Electrophysiol., 22(9), (Sep. 1999), 1372-7.
Leclercq, C, et al., "Hemodynamic importance of preserving the normal sequence of ventricular activation in permanent cardiac pacing", Am Heart J., 129(6), (Jun. 1995), 1133-41.
Levy, M. N., et al., "Effects of Repetitive Bursts of Vagal Activity on Heart Rate", Circulation Research, 30(2), (1972), 186-195.
Li, M., et al., "Vagal nerve stimulation markedly improves long-term survival after chronic heart failure in rats", Circulation, 109(1), (2004), 120-124.
Libbus, I., et al., "Method and Apparatus for Synchronizing Neural Simulation to Cardiac Cycles", U.S. Appl. No. 11/099,141, filed Apr. 5, 2005, 36 pgs.
Libbus, I., et al., "System and Method for Closed-Loop Neural Stimulation", U.S. Appl. No. 10/992,319, filed Nov. 18, 2004, 50 pgs.
Libbus, Imad, "Automatic Baroreflex Modulation Based on Cardiac Activity", U.S. Appl. No. 10/746,846, filed Dec. 24, 2003, 75 pgs.
Libbus, Imad, "Baroreflex Therapy for Disordered Breathing", U.S. Appl. No. 10/864,070, filed Jun. 8, 2004, 71 pgs.
Libbus, Imad, "Cardiac Rhythm Management Device With Neural Sensor", U.S. Appl. No. 10/992,320, filed Nov. 18, 2004, 65 pgs.
Libbus, Imad, "Method and Apparatus for Simultaneously Presenting Cardiac and Neural Signals", U.S. Appl. No. 11/114,246, filed Apr. 25, 2005, 58 pgs.
Libbus, Imad, "Neural Stimulation With Avoidance of Inappropriate Stimulation", U.S. Appl. No. 11/000,249, filed Nov. 30, 2004, 45 pgs.
Libbus, Imad, "Stimulator for Auricular Branch of Vagus Nerve", U.S. Appl. No. 11/005,703, filed Dec. 7, 2004, 35 pgs.
Libbus, Imad, "System and Method to Deliver Therapy in Presence of Another Therapy", U.S. Appl. No. 11/125,503, filed May 10, 2005, 39 pgs.
Libbus, Imad, "System to Provide Myocardial and Neural Stimulation", U.S. Appl. No. 11/087,935, filed Mar. 23, 2005, 52 pgs.
Mannheimer, C, et al., "Epidural spinal electrical stimulation in severe angina pectoris", British Heart Journal, 59(1), (Jan. 1988), 56-61.
Mannheimer, C, et al., "Transcutaneous electrical nerve stimulation (TENS) in angina pectoris", Pain, 26(3), (Sep. 1986), 291-300.

(56) References Cited

OTHER PUBLICATIONS

Mannheimer, C, et al., "Transcutaneous electrical nerve stimulation in severe angina pectoris", European Heart Journal, 3(4), (Aug. 1982), 297-302.
Martin, P., "Time-dependent heart period and contractility responses to successive brief vagal stimuli", Am J Physiol, 239(4), (Oct. 1980), H494-H500.
Mazgalev, T N, et al., "Autonomic modification of the atrioventricular node during atrial fibrillation: role in the slowing of ventricular rate", Circulation, 99(21), (Jun. 1, 1999), 2806-14.
Millar-Craig, M W, et al., "Circadian variation of blood-pressure", Lancet, 1(8068), (Apr. 15, 1978), 795-7.
Minisi, A J, et al., "Regional left ventricular deafferentation increases baroreflex sensitivity following myocardial infarction", Cardiovasc Res., 58(1), (Apr. 1, 2003), 136-41.
Moffitt, Julia, "Combined Neural Stimulation and Cardiac Resynchronization Therapy", U.S. Appl. No. 11/078,460, filed Mar. 11, 2005, 35 pgs.
Murphy, D F, et al., "Intractable angina pectoris: management with dorsal column stimulation", Medical Journal of Australia, 146(5), (Mar. 2, 1987), 260.
Neistadt, A, et al., "Effects of electrical stimulation of the carotid sinus nerve in reversal of experimentally induced hypertension", Surgery, 61(6), (Jun. 1967), 923-31.
Nolan, J., et al., "Prospective Study of Heart Rate Variability and Mortality in Chronic Heart Failure: Results of the United Kingdom Heart Failure Evaluation and Assessment of Risk Trial (UK-Heart).", Circulation, 98(15), (1998), 1510-1516.
Pastore, Joseph M., et al., "Multi-Site Ventricular Pacing Therapy With Parasympathetic Stimulation", U.S. Appl. No. 10/700,368, filed Nov. 3, 2003, 18 pgs.
Peters, T K, et al., "Temporal and spatial summation caused by aortic nerve stimulation in rabbits. Effects of stimulation frequencies and amplitudes", Journal of the Autonomic Nervous System, 27(3), (Aug. 1989), 193-205.
Peters, T K, et al., "The principle of electrical carotid sinus nerve stimulation: a nerve pacemaker system for angina pectoris and hypertension therapy", Annals of Biomedical Engineering, 8(4-6), (1980), 445-458.
Philbin, D M, et al., "Inappropriate shocks delivered by an ICD as a result of sensed potentials from a transcutaneous electronic nerve stimulation unit", Pacing & Clinical Electrophysiology, 21(10), (Oct. 1998), 2010-1.
Prakash, P, et al., "Asymmetrical distribution of aortic nerve fibers in the pig", Anat Rec., 158(1), (May 1967), 51-7.
Rosenqvist, M, et al., "The effect of ventricular activation sequence on cardiac performance during pacing", Pacing and Electrophysiology, 19(9), (1996), 1279-1286.
Rushmer, Robert F, "Chapter 5—Systemic Arterial Pressure", in: Cardiovascular dynamics, Philadelphia : Saunders, (1976), 176-216.
Schauerte, P, et al., "Catheter stimulation of cardiac parasympathetic nerves in humans: a novel approach to the cardiac autonomic nervous system", Circulation, 104(20), (Nov. 13, 2001), 2430-5.
Schauerte, P, et al., "Ventricular rate control during atrial fibrillation by cardiac parasympathetic nerve stimulation: a transvenous approach", J Am Coll Cardiol., 34(7), (Dec. 1999), 2043-50.
Schauerte, P. N, et al., "Transvenous parasympathetic cardiac nerve stimulation: an approach for stable sinus rate control", Journal of Cardiovascular Electrophysiology, 10(11), (Nov. 1999), 1517-1524.
Schauerte, P., et al., "Transvenous parasympathetic nerve stimulation in the inferior vena cava and atrioventricular conduction", Journal of Cardiovascular Electrophysiology, 11(1), (Jan. 2000), 1 pg.
Scherlag, M A., et al., "Endovascular Neural Stimulation via a Novel Basket Electrode Catheter: Comparison of Electrode Configurations", Journal of Interventional Cardiac Electrophysiology, 4(1), (Apr. 2000), 219-224.
Sigurdsson, A., et al., "The Role of Neurohormonal Activation in Chronic Heart Failure and Postmyocardial Infarction", American Heart Journal, 132(1, Part 2), (Jul. 1996), 229-234.
Takahashi, N, et al., "Vagal modulation of ventricular tachyarrhythmias induced by left ansae subclaviae stimulation in rabbits", Japanese Heart Journal, 39(4), (Jul. 1998), 503-11.
Tse, H F, et al., "Long-term effect of right ventricular pacing on myocardial perfusion and function", J Am Coll Cardiol., 29(4), (Mar. 15, 1997), 744-9.
Vanoli, E., et al., "Vagal Stimulation and Prevention of Sudden Death in Conscious Dogs With a Healed Myocardial Infarction", Circulation Research, 68(5), (May 1991), 1471-1481.
Veerman, D P, et al., "Circadian profile of systemic hemodynamics", Hypertension, 26(1), (Jul. 1995), 55-9.
Verity, M A, et al., "Plurivesicular nerve endings in the pulmonary artery", Nature, 211(48), (Jul. 30, 1966), 537-8.
Verity, M, et al., "Pulmonary artery innervation: a morphopharmacologic correlation", Proceedings of the Western Pharmacology Society, 8, (1965), 57-9.
Wallick, D W, et al., "Selective AV nodal vagal stimulation improves hemodynamics during acute atrial fibrillation in dogs", American Journal of Physiology—Heart & Circulatory Physiology, 281(4), (Oct. 2001), H1490-7.
Waninger, M S, et al., "Electrophysiological control of ventricular rate during atrial fibrillation", Pacing & Clinical Electrophysiology, 23(8), (Aug. 2000), 1239-44.
Wiggers, C J, et al., "The muscular reactions of the mammalian ventricles to artificial surface stimuli", American Journal of Physiology, (1925), 346-378.
Zhang, Y, et al., "Optimal ventricular rate slowing during atrial fibrillation by feedback AV nodal-selective vagal stimulation", American Journal of Physiology—Heart & Circulatory Physiology, 282(3), (Mar. 2002), H1102-10.
Zhou, X, et al., "Prevention of high incidence of neurally mediated ventricular arrhythmias by afferent nerve stimulation in dogs", Circulation, 101(7), (Feb. 22, 2000), 819-24.
U.S. Appl. No. 10/962,845, U.S. Pat. No. 8,175,705, filed Oct. 12, 2004, System and Method for Sustained Baroreflex Stimulation.
U.S. Appl. No. 13/459,669, filed Apr. 30, 2012, System and Method for Sustained Baroreflex Stimulation.
U.S. Appl. No. 15/465,425, filed Mar. 21, 2017, System and Method for Sustained Baroreflex Stimulation.
U.S. Appl. No. 11/099,141, U.S. Pat. No. 7,542,800, filed Apr. 5, 2005, Method and Apparatus for Synchronizing Neural Stimulation to Cardiac Cycles.
U.S. Appl. No. 12/469,012, U.S. Pat. No. 8,452,398, filed May 20, 2009, Method and Apparatus for Synchronizing Neural Stimulation to Cardiac Cycles.
U.S. Appl. No. 13/898,069, filed May 20, 2013, Method and Apparatus for Synchronizing Neural Stimulation to Cardiac Cycles.

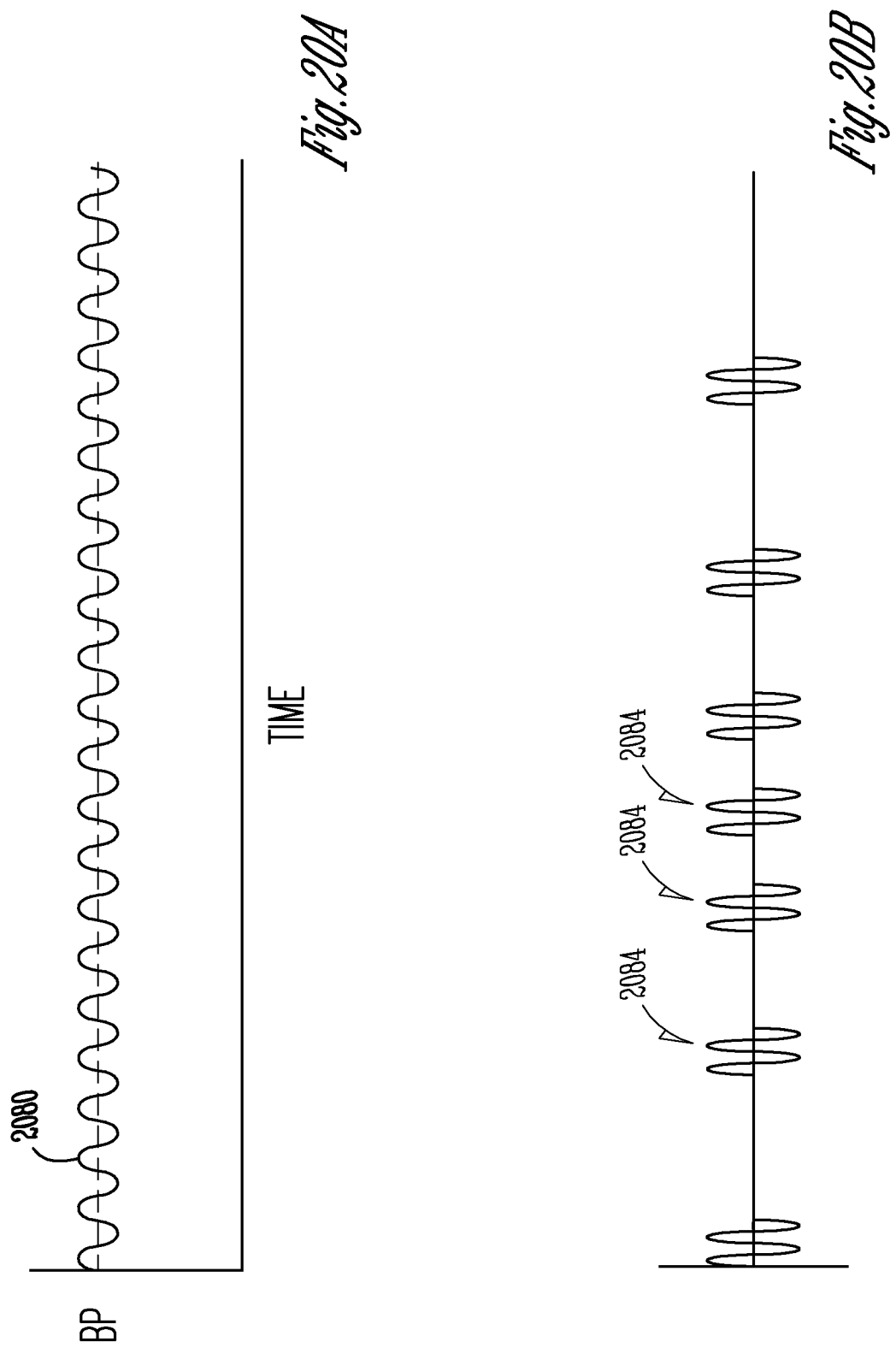

SYSTEM AND METHOD FOR SUSTAINED BAROREFLEX STIMULATION

CLAIM OF PRIORITY

This application is a continuation of U.S. application Ser. No. 15/465,425, filed Mar. 21, 2017, which is a continuation of U.S. application Ser. No. 13/459,669, filed Apr. 30, 2012, which is a continuation of and claims the benefit of priority under 35 U.S.C. § 120 to U.S. patent application Ser. No. 10/962,845, filed on Oct. 12, 2004, now issued as U.S. Pat. No. 8,175,705, all of which are hereby incorporated by reference herein in their entirety.

TECHNICAL FIELD

This application relates generally to neural stimulators and, more particularly, to systems, devices and methods for sustaining baroreflex stimulation.

BACKGROUND

Implanting a chronic electrical stimulator, such as a cardiac stimulator, to deliver medical therapy(ies) is known. Examples of cardiac stimulators include implantable cardiac rhythm management (CRM) devices such as pacemakers, implantable cardiac defibrillators (ICDs), and implantable devices capable of performing pacing and defibrillating functions.

Implantable CRM devices provide electrical stimulation to selected chambers of the heart in order to treat disorders of cardiac rhythm. An implantable pacemaker, for example, is a CRM device that paces the heart with timed pacing pulses. If functioning properly, the pacemaker makes up for the heart's inability to pace itself at an appropriate rhythm in order to meet metabolic demand by enforcing a minimum heart rate. Some CRM devices synchronize pacing pulses delivered to different areas of the heart in order to coordinate the contractions. Coordinated contractions allow the heart to pump efficiently while providing sufficient cardiac output.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Hypertension is a cause of heart disease and other related cardiac co-morbidities. Hypertension occurs when blood vessels constrict. As a result, the heart works harder to maintain flow at a higher blood pressure, which can contribute to heart failure. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

A pressoreceptive region or field is capable of sensing changes in pressure, such as changes in blood pressure. Pressoreceptor regions are referred to herein as baroreceptors, which generally include any sensors of pressure changes. For example, baroreceptors include sensory nerve endings that are sensitive to the stretching of the wall that results from increased blood pressure from within, and function as the receptor of a central reflex mechanism that tends to reduce the pressure. Baroreflex functions as a negative feedback system, and relates to a reflex mechanism triggered by stimulation of a baroreceptor. Additionally, baroreflex can be triggered by stimulation of afferent nerves. Increased pressure stretches blood vessels, which in turn activates baroreceptors in the vessel walls. Activation of baroreceptors naturally occurs through internal pressure and stretching of the arterial wall, causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance.

The general concept of stimulating afferent nerve trunks leading from baroreceptors is known. For example, direct electrical stimulation has been applied to the vagal nerve and carotid sinus. Research has indicated that electrical stimulation of the carotid sinus nerve can result in reduction of experimental hypertension, and that direct electrical stimulation to the pressoreceptive regions of the carotid sinus itself brings about reflex reduction in experimental hypertension. Research further has indicated that the baroreflex quickly adapts to increased baroreflex stimulation. Electrical systems have been proposed to treat hypertension in patients who do not otherwise respond to therapy involving lifestyle changes and hypertension drugs, and possibly to reduce drug dependency for other patients.

The baroreflex adapts to increased baroreflex stimulation. Static or constant baroreflex stimulation causes a quick or immediate response which gradually diminishes. Over time, the baroreflex resets and returns to the baseline response, which renders static stimulation ineffective. Thus, baroreflex adaptation poses a problem for sustaining baroreflex therapy that effectively inhibits SNA.

SUMMARY

Various aspects of the present subject matter provide an implantable medical device. In various embodiments, the device comprises a baroreflex stimulator and a controller. The baroreflex stimulator is adapted to generate a stimulation signal to stimulate a baroreflex. The controller is adapted to communicate with the baroreflex stimulator and implement a baroreflex stimulation protocol to vary an intensity of the baroreflex stimulation provided by the stimulation signal to abate baroreflex adaptation. According to various embodiments, the controller is adapted to implement the baroreflex stimulation protocol to periodically modulate the baroreflex stimulation to produce an effect that mimics an effect of pulsatile pressure.

Various aspects and embodiments of the present subject matter provide an implantable medical system, comprising means for generating a baroreflex stimulation signal to stimulate a baroreflex, and means for abating baroreflex adaptation, including means for periodically changing at least one parameter of the baroreflex stimulation signal such that the baroreflex stimulation ranges within a range from a first baroreflex stimulation level and a second baroreflex stimulation level. According to various embodiments, the implantable medical system comprises a single implantable device; and according to various embodiments, the implantable medical system comprises an implantable neuro stimulator (NS) device and an implantable cardiac rhythm management (CRM) device.

Various aspects and embodiments of the present subject matter provide a method, comprising generating a baroreflex stimulation signal to stimulate a baroreflex, and abating baroreflex adaptation, including changing at least one parameter of the baroreflex stimulation signal such that the baroreflex stimulation ranges within a range from a first baroreflex stimulation level and a second baroreflex stimulation level. According to various embodiments, the baroreflex stimulation signal is modulated to mimic an effect of pulsatile pressure. In various embodiments, a frequency, an amplitude, and/or a duty cycle of the baroreflex stimulation signal are periodically changed.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIG. 20A illustrates a pulse and FIG. 20B illustrates an example of a burst frequency modulation protocol to mimic effects of pulsatile pressure.

DETAILED DESCRIPTION

Figure 1B:
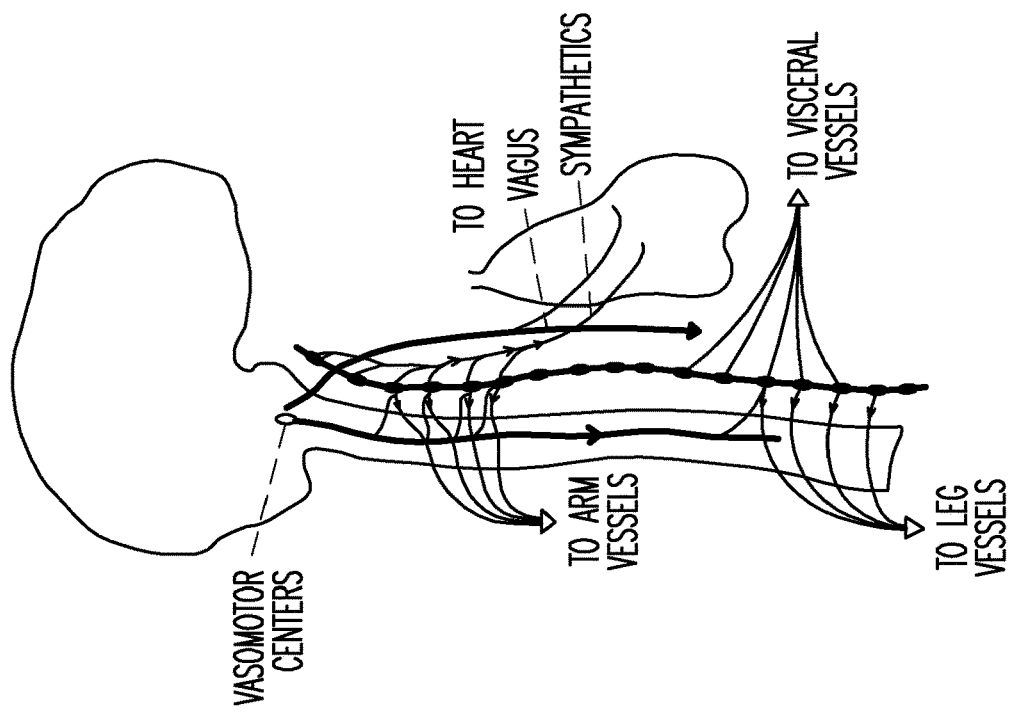
FIGS. 1A and 1B illustrate neural mechanisms for peripheral vascular control.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Hypertension and Baroreflex Physiology

A brief discussion of hypertension and the physiology related to baroreceptors is provided to assist the reader with understanding this disclosure. This brief discussion introduces hypertension, the autonomic nervous system, and baroreflex.

Hypertension is a cause of heart disease and other related cardiac co-morbidities. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Hypertension occurs when blood vessels constrict. As a result, the heart works harder to maintain flow at a higher blood pressure. Consequences of uncontrolled hypertension include, but are not limited to, retinal vascular disease and stroke, left ventricular hypertrophy and failure, myocardial infarction, dissecting aneurysm, and renovascular disease.

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system.

The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Figure 1A:
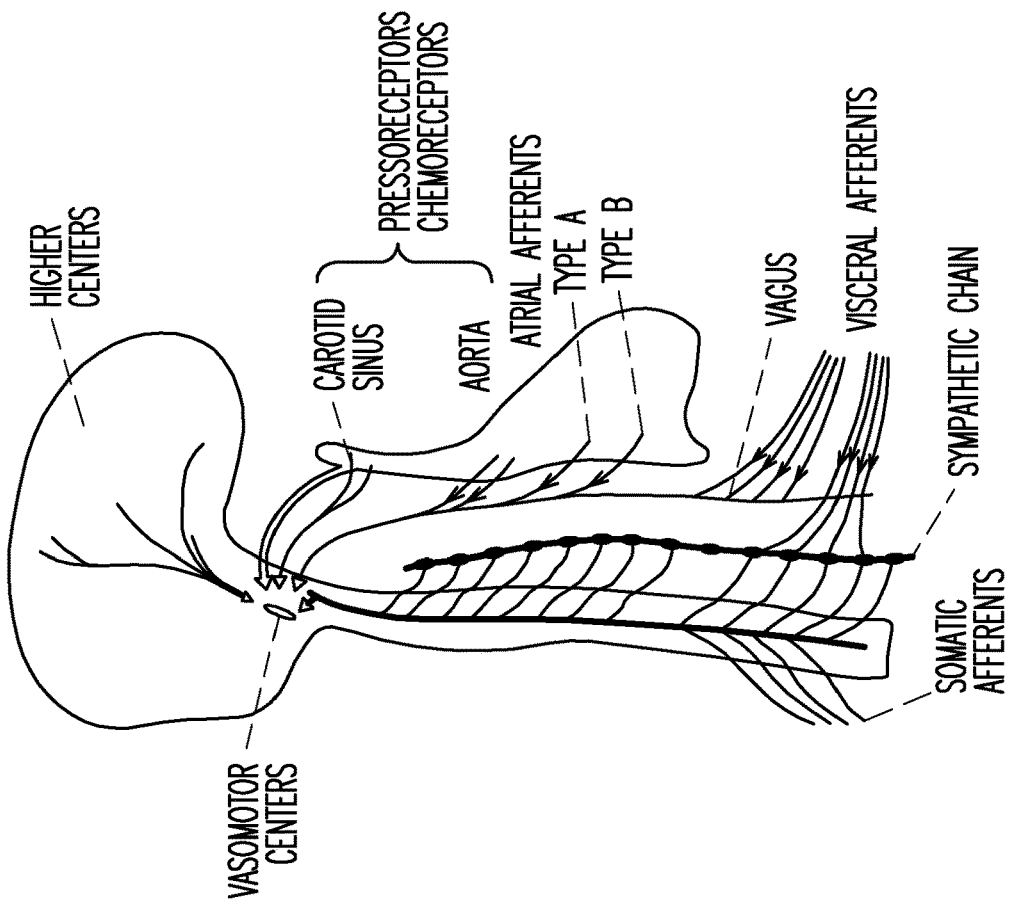

The subject matter of this disclosure generally refers to the effects that the ANS has on the heart rate and blood pressure, including vasodilation and vasoconstriction. The heart rate and force is increased when the sympathetic nervous system is stimulated, and is decreased when the sympathetic nervous system is inhibited (the parasympathetic nervous system is stimulated). FIGS. 1A and 1B illustrate neural mechanisms for peripheral vascular control. FIG. 1A generally illustrates afferent nerves to vasomotor centers. An afferent nerve conveys impulses toward a nerve center. A vasomotor center relates to nerves that dilate and constrict blood vessels to control the size of the blood vessels. FIG. 1B generally illustrates efferent nerves from vasomotor centers. An efferent nerve conveys impulses away from a nerve center.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response, such as vasodilation, in one physiological system may also result in an undesired response in other physiological systems.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Clusters of nerve cells can be referred to as autonomic ganglia. These nerve cells can also be electrically stimulated to induce a baroreflex, which inhibits the sympathetic nerve activity and stimulates parasympathetic nerve activity. Autonomic ganglia thus forms part of a baroreflex pathway. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of vessel wall (e.g. arterial wall).

Some aspects of the present subject matter locally stimulate specific nerve endings in arterial walls rather than stimulate afferent nerve trunks in an effort to stimulate a desire response (e.g. reduced hypertension) while reducing the undesired effects of indiscriminate stimulation of the nervous system. For example, some embodiments stimulate baroreceptor sites in the pulmonary artery. Some embodiments of the present subject matter involve stimulating baroreceptor sites or nerve endings in the aorta and the chambers of the heart, and some embodiments of the present subject matter involve stimulating an afferent nerve trunk, such as the vagus, carotid and aortic nerves. Some embodiments stimulate afferent nerve trunks using a cuff electrode, and some embodiments stimulate afferent nerve trunks using an intravascular lead positioned in a blood vessel proximate to the nerve, such that the electrical stimulation passes through the vessel wall to stimulate the afferent nerve trunk.

Figure 2:
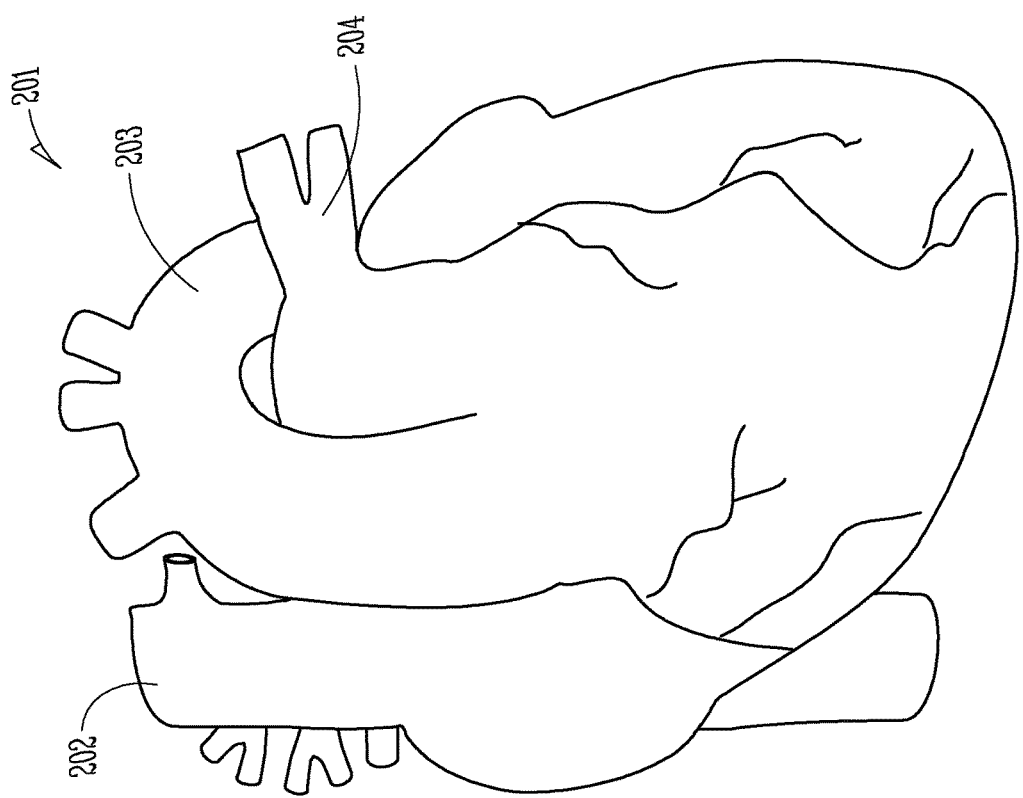
FIG. 2 illustrates a heart.

FIG. 2 illustrates a heart. The heart 201 includes a superior vena cava 202, an aortic arch 203, and a pulmonary artery 204, and is useful to provide a contextual relationship with the illustrations in FIGS. 3-5. As is discussed in more detail below, the pulmonary artery 204 includes baroreceptors. A lead is capable of being intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. A portion of the pulmonary artery and aorta are proximate to each other. Various embodiments stimulate baroreceptors in the aorta using a lead intravascularly positioned in the pulmonary artery. Thus, according to various aspects of the present subject matter, the baroreflex is stimulated in or around the pulmonary artery by at least one electrode intravascularly inserted into the pulmonary artery. Alternatively, a wireless stimulating device, with or without pressure sensing capability, may be positioned via catheter into the pulmonary artery. Control of stimulation and/or energy for stimulation may be supplied by another implantable or external device via ultrasonic, electromagnetic or a combination thereof. Aspects of the present subject matter provide a relatively noninvasive surgical technique to implant a baroreflex stimulator intravascularly into the pulmonary artery.

Figure 3:
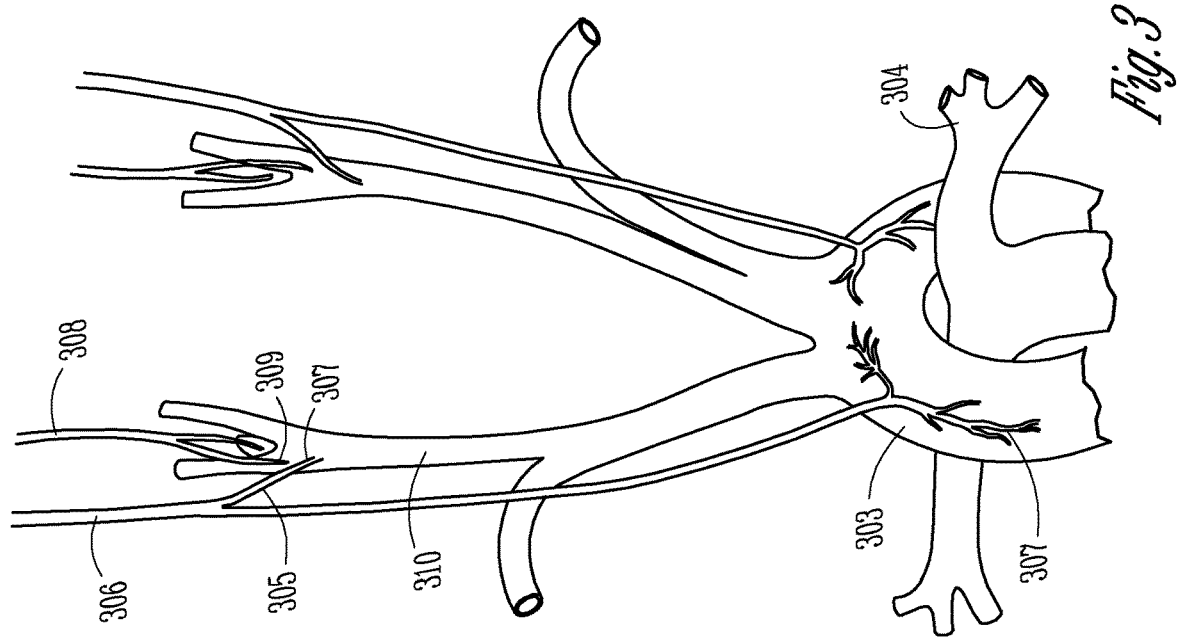
FIG. 3 illustrates baroreceptors and afferent nerves in the area of the carotid sinuses and aortic arch.

FIG. 3 illustrates baroreceptors in the area of the carotid sinus 305, aortic arch 303 and pulmonary artery 304. The aortic arch 303 and pulmonary artery 304 were previously illustrated with respect to the heart in FIG. 2. As illustrated in FIG. 3, the vagus nerve 306 extends and provides sensory nerve endings 307 that function as baroreceptors in the aortic arch 303, in the carotid sinus 305 and in the common carotid artery 310. The glossopharyngeal nerve 308 provides nerve endings 309 that function as baroreceptors in the carotid sinus 305. These nerve endings 307 and 309, for example, are sensitive to stretching of the wall resulting from increased pressure from within. Activation of these nerve endings reduce pressure. Although not illustrated in the figures, the atrial and ventricular chambers of the heart also include baroreceptors. Cuffs have been placed around afferent nerve trunks, such as the vagal nerve, leading from baroreceptors to vasomotor centers to stimulate the baroreflex. According to various embodiments of the present subject matter, afferent nerve trunks can be stimulated using a cuff or intravascularly-fed lead positioned in a blood vessel proximate to the afferent nerves.

Figure 5:
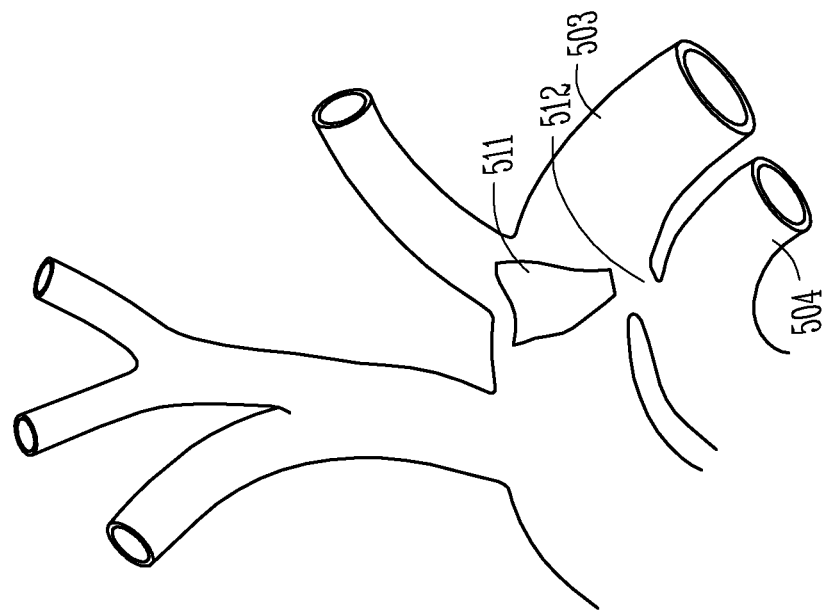
FIG. 5 illustrates baroreceptor fields in the aortic arch, the ligamentum arteriosum and the trunk of the pulmonary artery.
Figure 4:
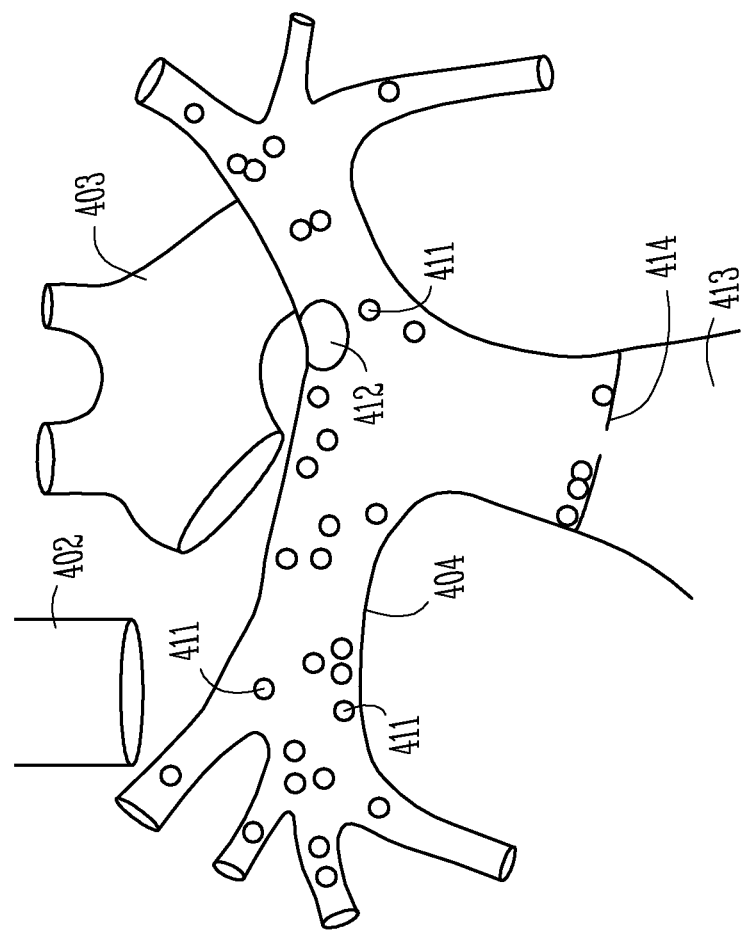
FIG. 4 illustrates baroreceptors in and around the pulmonary artery.

FIG. 4 illustrates baroreceptors in and around a pulmonary artery 404. The superior vena cava 402 and the aortic arch 403 are also illustrated. As illustrated, the pulmonary artery 404 includes a number of baroreceptors 411, as generally indicated by the dark area. Furthermore, a cluster of closely spaced baroreceptors is situated near the attachment of the ligamentum arteriosum 412. FIG. 4 also illustrates the right ventricle 413 of the heart, and the pulmonary valve 414 separating the right ventricle 413 from the pulmonary artery 404. According to various embodiments of the present subject matter, a lead is inserted through a peripheral vein and threaded through the tricuspid valve into the right ventricle, and from the right ventricle 413 through the pulmonary valve 414 and into the pulmonary artery 404 to stimulate baroreceptors in and/or around the pulmonary artery. In various embodiments, for example, the lead is positioned to stimulate the cluster of baroreceptors near the ligamentum arteriosum 412. FIG. 5 illustrates baroreceptor fields 511 in the aortic arch 503, near the ligamentum arteriosum 512 and the trunk of the pulmonary artery 504. Some embodiments position the lead in the pulmonary artery to stimulate baroreceptor sites in the aorta.

Figure 6:
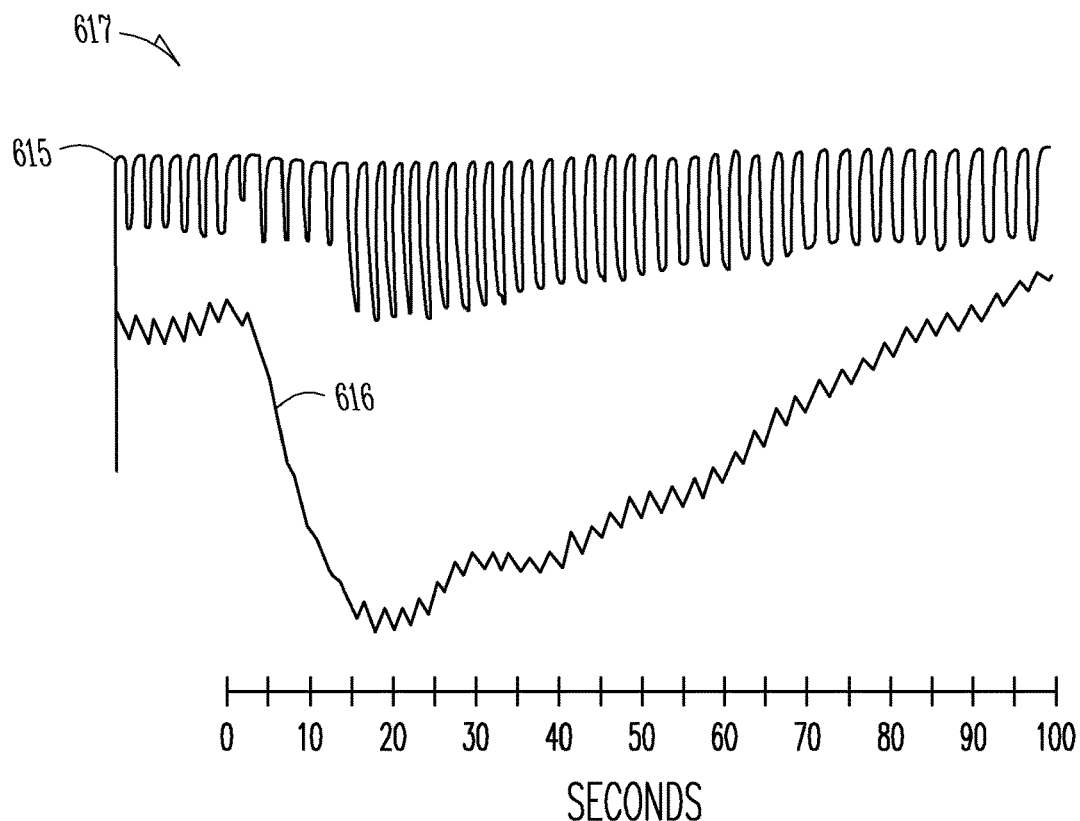
FIG. 6 illustrates a known relationship between respiration and blood pressure when the baroreflex is stimulated.

FIG. 6 illustrates a known relationship between respiration 615 and blood pressure 616 when the left aortic nerve is stimulated. When the nerve is stimulated at 617, the blood pressure 616 drops, and the respiration 615 becomes faster and deeper, as illustrated by the higher frequency and amplitude of the respiration waveform. The respiration and blood pressure appear to return to the pre-stimulated state in approximately one to two minutes after the stimulation is removed. This relationship between respiration and blood pressure allows respiration to be used as a surrogate parameter for blood pressure.

Figure 7:
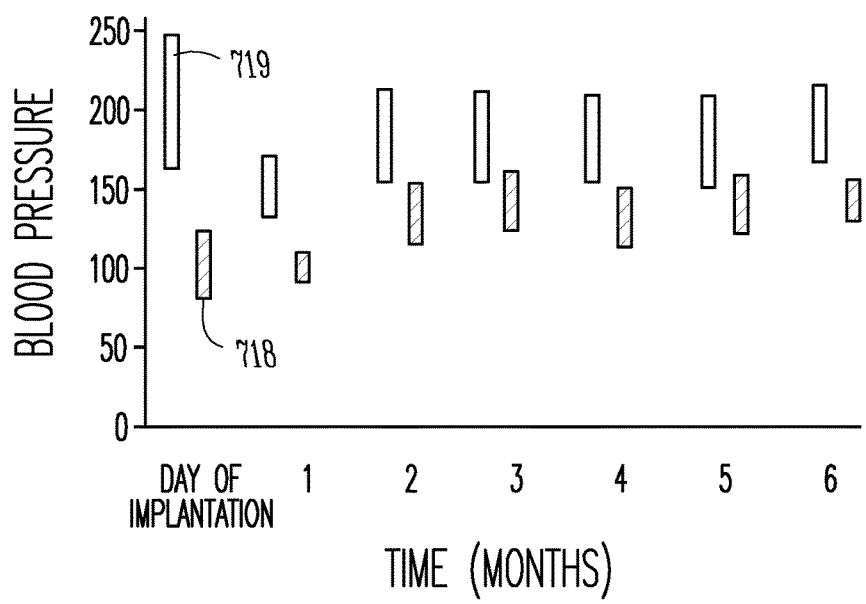
FIG. 7 illustrates a blood pressure response to carotid nerve stimulation in a hypertensive dog during 6 months of intermittent carotid nerve stimulation.

FIG. 7 illustrates a known blood pressure response to carotid nerve stimulation in a hypertensive dog during 6 months of intermittent carotid nerve stimulation. The carotid nerve stimulation involved turning on a carotid nerve stimulator once a month for up to six hours, and measuring the blood pressure response to monitor the stability of the acute response over long time periods. The figure illustrates that the blood pressure of a stimulated dog 718 is significantly less than the blood pressure of a control dog 719 that also has high blood pressure. Thus, such stimulation is capable of triggering the baroreflex to reduce high blood pressure.

Baroreflex Stimulator Systems

Various embodiments of the present subject matter relate to baroreflex stimulator systems. Such baroreflex stimulation systems are also referred to herein as neural stimulator (NS) devices or components. Examples of neural stimulators include anti-hypertension (AHT) devices or AHT components that are used to treat hypertension. Various embodiments of the present subject matter include stand-alone implantable baroreflex stimulator systems, include implantable devices that have integrated NS and cardiac rhythm management (CRM) components, and include systems with at least one implantable NS device and an implantable CRM device capable of communicating with each other either wirelessly or through a wire lead connecting the implantable devices. Although implantable systems are illustrated and discussed, various aspects and embodiments of the present subject matter can be implemented in external NS devices. Integrating NS and CRM functions that are either performed in the same or separate devices improves aspects of the NS therapy and cardiac therapy by allowing these therapies to intelligently work together.

Figure 8:
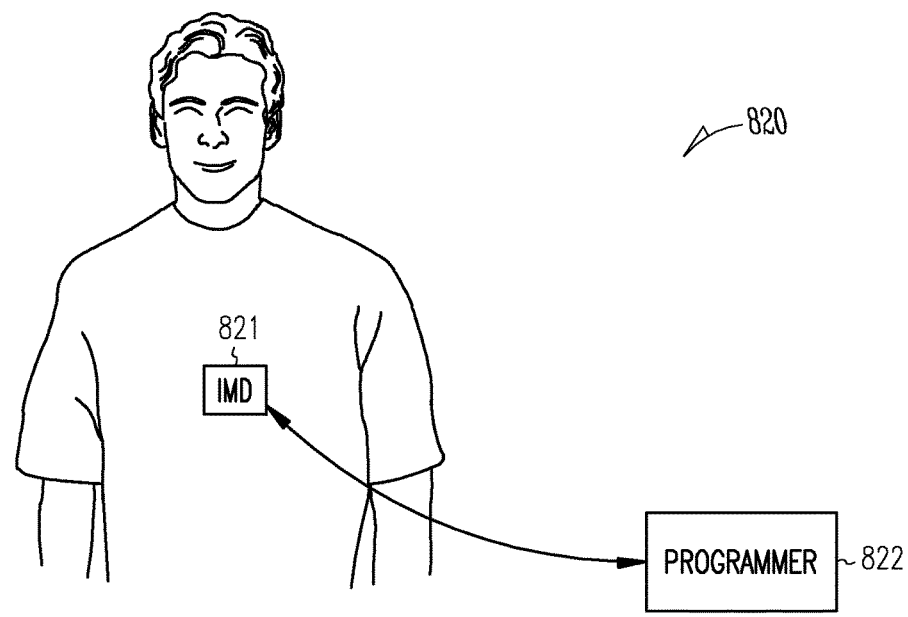
FIG. 8 illustrates a system including an implantable medical device (IMD) and a programmer, according to various embodiments of the present subject matter.

FIG. 8 illustrates a system 820 including an implantable medical device (IMD) 821 and a programmer 822, according to various embodiments of the present subject matter. Various embodiments of the IMD 821 include neural stimulator functions only, and various embodiments include a combination of NS and CRM functions. Some embodiments of the neural stimulator provide AHT functions to treat hypertension. The programmer 822 and the IMD 821 are capable of wirelessly communicating data and instructions. In various embodiments, for example, the programmer 822 and IMD 821 use telemetry coils to wirelessly communicate data and instructions. Thus, the programmer can be used to adjust the programmed therapy provided by the IMD 821, and the IMD can report device data (such as battery and lead resistance) and therapy data (such as sense and stimulation data) to the programmer using radio telemetry, for example. According to various embodiments, the IMD 821 stimulates baroreceptors to provide NS therapy such as AHT therapy. Various embodiments of the IMD 821 stimulate baroreceptors in the pulmonary artery using a lead fed through the right ventricle similar to a cardiac pacemaker lead, and further fed into the pulmonary artery. Other embodiments stimulate other baroreceptor sites or baroreflex pathways. According to various embodiments, the IMD 821 includes a sensor to sense ANS activity. Such a sensor can be used to perform feedback in a closed loop control system. For example, various embodiments sense surrogate parameters, such as respiration and blood pressure, indicative of ANS activity. According to various embodiments, the IMD further includes cardiac stimulation capabilities, such as pacing and defibrillating capabilities in addition to the capabilities to stimulate baroreceptors and/or sense ANS activity.

Figure 9:
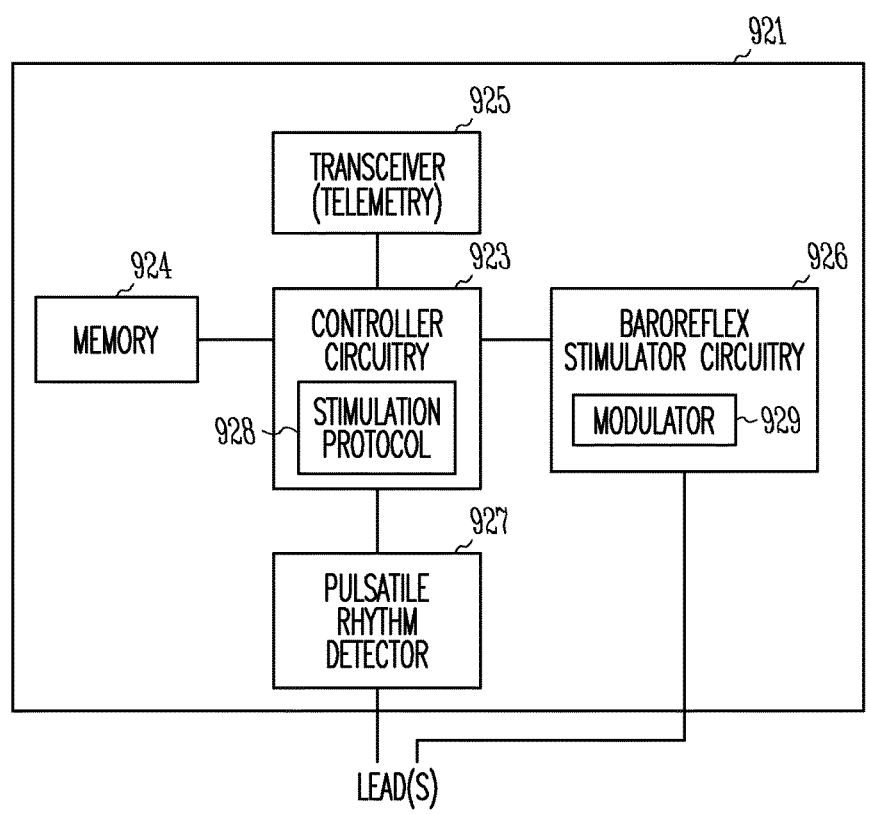
FIG. 9 illustrates an implantable medical device (IMD) such as shown in the system of FIG. 8, according to various embodiments of the present subject matter.

FIG. 9 illustrates an implantable medical device (IMD) 921 such as the IMD 821 shown in the system 820 of FIG. 8, according to various embodiments of the present subject matter. The illustrated IMD 921 performs NS functions. Some embodiments of the illustrated IMD 921 performs an AHT function to treat hypertension, and thus illustrates an implantable AHT device. The illustrated device 921 includes controller circuitry 923 and a memory 924. The controller circuitry 923 is capable of being implemented using hardware, software, and combinations of hardware and software. For example, according to various embodiments, the controller circuitry 923 includes a processor to perform instructions embedded in the memory 924 to perform functions associated with NS therapy such as AHT therapy. The memory 924 includes instructions that correspond to a baroreflex stimulation protocol 928. The controller executes these instructions to implement the baroreflex stimulation protocol. For example, the illustrated device 921 further includes a transceiver 925 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device 921 further includes baroreflex stimulation circuitry 926 to stimulate a baroreflex by stimulating a baroreceptor or baroreflex pathway such as afferent nerves. Various embodiments of the device 921 also includes sensor circuitry 927, illustrated as a pulsatile rhythm detector to detect pulsatile parameters, according to various aspects and embodiments of the present subject matter. One or more leads are able to be connected to the sensor circuitry 927 and baroreflex stimulation circuitry 926. The baroreflex stimulation circuitry 926 is used to apply electrical stimulation pulses to induce a baroreflex at desired baroreceptors sites, such as baroreceptor sites in the pulmonary artery, and/or desired baroreflex pathway sites, such as afferent nerves, through one or more stimulation electrodes. In various embodiments, the sensor circuitry 927 is further adapted to detect and process ANS nerve activity and/or surrogate parameters such as blood pressure, respiration and the like, to determine the ANS activity and provide closed loop feedback control.

According to various embodiments, the stimulator circuitry 926 includes a modulator 929 to modulate any one or any combination of two or more of the following pulse features: the amplitude of the stimulation pulse, the frequency of the stimulation pulse, the burst frequency or duty cycle of the pulse. Various embodiments provide stimulation signals having a morphology of a square wave, a sinusoidal wave, a triangle wave and/or a wave that has appropriate harmonic components to mimic white noise such as is indicative of naturally-occurring baroreflex stimulation.

Figure 10:
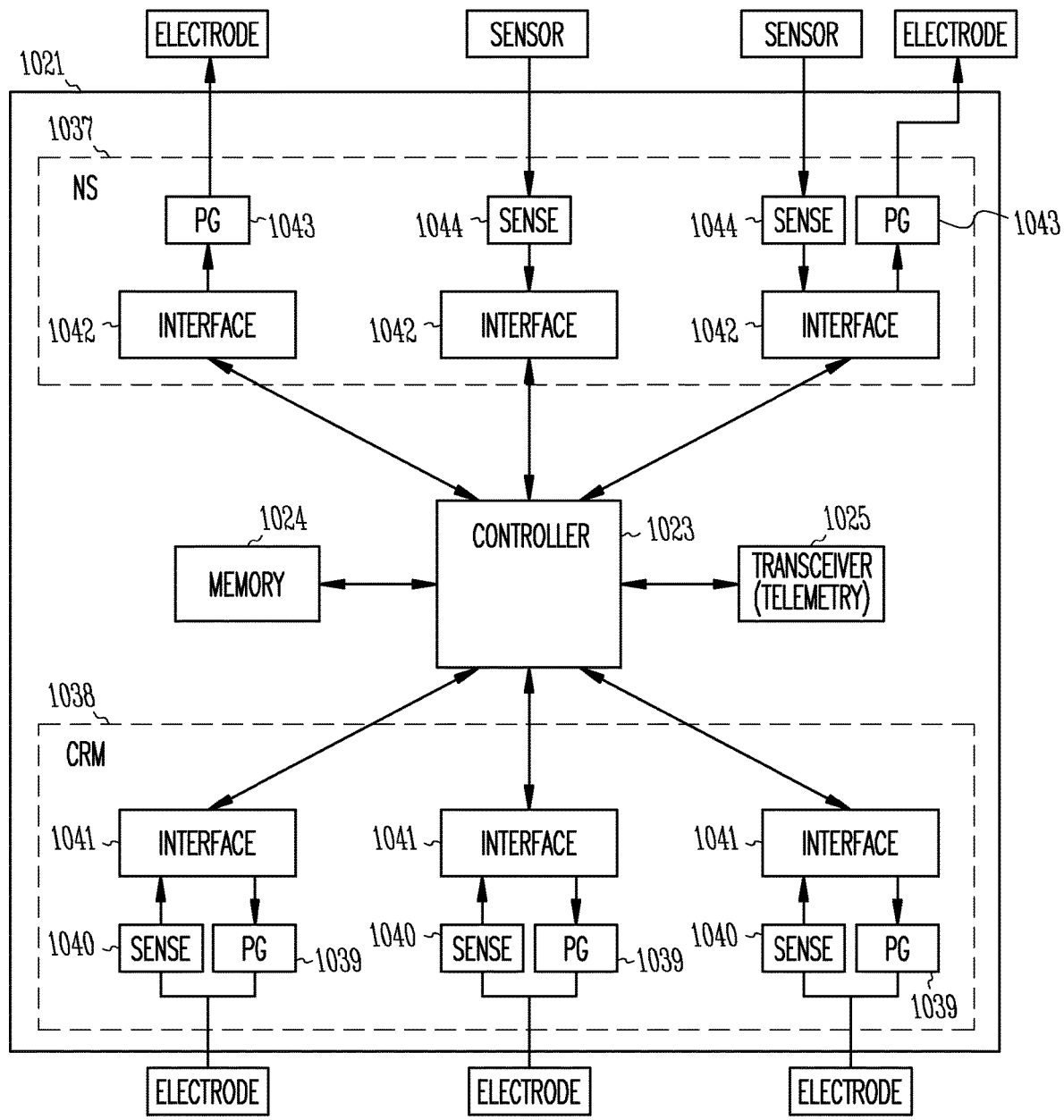
FIG. 10 illustrates an implantable medical device (IMD) such as shown in FIG. 8 having a neural stimulator (NS) component and cardiac rhythm management (CRM) component, according to various embodiments of the present subject matter.

FIG. 10 illustrates an implantable medical device (IMD) 1021 such as shown at 821 in FIG. 8 having a neural stimulation (NS), such as an anti-hypertension (AHT) component 1037 to treat hypertension, and cardiac rhythm management (CRM) component 1038, according to various embodiments of the present subject matter. The illustrated device 1021 includes a controller 1023 and a memory 1024. According to various embodiments, the controller 1023 includes hardware, software, or a combination of hardware and software to perform the baroreflex stimulation and CRM functions. For example, the programmed therapy applications discussed in this disclosure are capable of being stored as computer-readable instructions embodied in memory and executed by a processor. According to various embodiments, the controller 1023 includes a processor to execute instructions embedded in memory to perform the baroreflex stimulation and CRM functions. The illustrated device 1021 further includes a transceiver 1025 and associated circuitry for use to communicate with a programmer or another external or internal device. Various embodiments include a telemetry coil.

The CRM therapy section 1038 includes components, under the control of the controller, to stimulate a heart and/or sense cardiac signals using one or more electrodes. The CRM therapy section includes a pulse generator 1039 for use to provide an electrical signal through an electrode to stimulate a heart, and further includes sense circuitry 1040 to detect and process sensed cardiac signals or otherwise detect pulsatile parameters according to the present subject matter. An interface 1041 is generally illustrated for use to communicate between the controller 1023 and the pulse generator 1039 and sense circuitry 1040. Three electrodes are illustrated as an example for use to provide CRM therapy. However, the present subject matter is not limited to a particular number of electrode sites. One or more electrodes can be positioned on a lead, and one or more leads can be used. Each electrode may include its own pulse generator and sense circuitry. However, the present subject matter is not so limited. The pulse generating and sensing functions can be multiplexed to function with multiple electrodes.

The NS therapy section 1037 includes components, under the control of the controller, to stimulate a baroreceptor and/or sense ANS parameters associated with nerve activity or surrogates of ANS parameters such as blood pressure and respiration. Three interfaces 1042 are illustrated for use to provide ANS therapy. However, the present subject matter is not limited to a particular number interfaces, or to any particular stimulating or sensing functions. Pulse generators 1043 are used to provide electrical pulses to an electrode for use to stimulate a baroreceptor site. According to various embodiments, the pulse generator includes circuitry to set, and in some embodiments change, the amplitude of the stimulation pulse, the frequency of the stimulation pulse, the burst frequency of the pulse, and/or the morphology of the pulse such as a square wave, triangle wave, sinusoidal wave, and waves with desired harmonic components to mimic white noise or other signals. Sense circuits 1044 are used to detect and process signals from a sensor, such as a sensor of pulsatile parameters, and/or a sensor of nerve activity, blood pressure, respiration, and the like. The interfaces 1042 are generally illustrated for use to communicate between the controller 1023 and the pulse generator 1043 and sense circuitry 1044. Each interface, for example, may be used to control a separate lead. Various embodiments of the NS therapy section only include a pulse generator to stimulate baroreceptors. The NS therapy section is capable of providing AHT therapy to treat hypertension, for example.

An aspect of the present subject matter relates to a chronically-implanted stimulation system specially designed to treat hypertension by monitoring blood pressure and periodically stimulating baroreceptors or a baroreflex pathway using a stimulation protocol to activate the baroreflex and inhibit sympathetic discharge from the vasomotor center. Baroreceptors are located in various anatomical locations such as the carotid sinus and the aortic arch. Other baroreceptor locations include the pulmonary artery, including the ligamentum arteriosum, and sites in the atrial and ventricular chambers. Other baroreflex stimulation locations include baroreflex pathways such as ganglia in cardiac fat pads and afferent nerve trunks. In various embodiments, the system is integrated into a pacemaker/defibrillator or other electrical stimulator system. Components of the system include a pulse generator, sensors to monitor blood pressure or other pertinent physiological parameters, leads to apply electrical stimulation to baroreceptors, algorithms to determine the appropriate time to administer stimulation, and algorithms to manipulate data for display and patient management.

Various embodiments relate to a system that seeks to deliver electrically mediated NS therapy, such as AHT therapy, to patients. Various embodiments combine a "stand-alone" pulse generator with a minimally invasive, lead that stimulates baroreceptors and/or baroreflex pathways in the vicinity of the heart, such as in the pulmonary artery or cardiac fat pad(s), using direct or transvenous stimulation, for example. This embodiment is such that general medical practitioners lacking the skills of specialist can implant it. Various embodiments incorporate a simple implanted system that can sense parameters indicative of blood pressure. This system adjusts the therapeutic output (waveform amplitude, frequency, etc.) so as to maintain a desired quality of life. In various embodiments, an implanted system includes a pulse generating device and lead system, the stimulating electrode of which is positioned near endocardial baroreceptor tissues using transvenous implant technique(s). Another embodiment includes a system that combines NS therapy with traditional bradyarrhythmia, tachyarrhythmia, and/or congestive heart failure (CHF) therapies. Some embodiments use an additional "baroreflex lead" that emerges from the device header and is paced from a modified traditional pulse generating system. In another embodiment, a traditional CRM lead is modified to incorporate proximal electrodes that are naturally positioned near baroreceptor sites. With these leads, distal electrodes provide CRM therapy and proximate electrodes stimulate baroreceptors.

A system according to these embodiments can be used to augment partially successful treatment strategies. As an example, undesired side effects may limit the use of some pharmaceutical agents. The combination of a system according to these embodiments with reduced drug doses may be particularly beneficial.

According to various embodiments, the lead(s) and the electrode(s) on the leads are physically arranged with respect to the heart in a fashion that enables the electrodes to properly transmit pulses and sense signals from the heart, and with respect to baroreceptors to stimulate the baroreflex. As there may be a number of leads and a number of electrodes per lead, the configuration can be programmed to use a particular electrode or electrodes. According to various embodiments, the baroreflex is stimulated by stimulating afferent nerve trunks.

Figure 11:
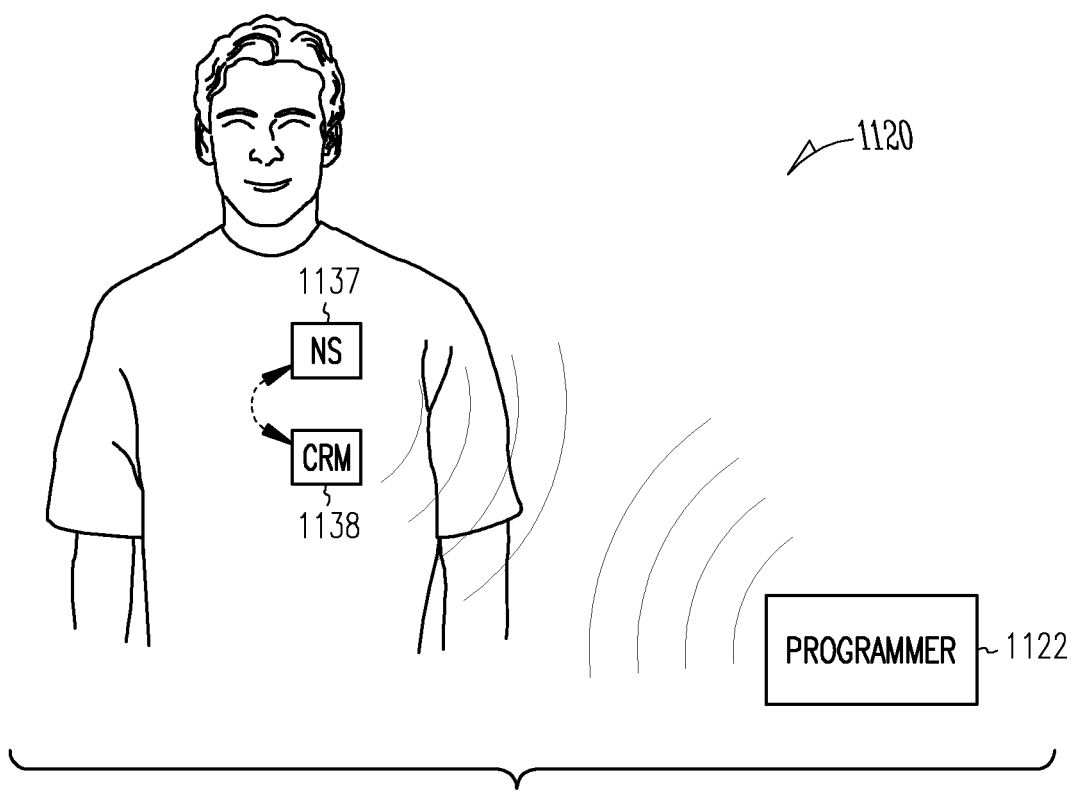
FIG. 11 illustrates a system including a programmer, an implantable neural stimulator (NS) device and an implantable cardiac rhythm management (CRM) device, according to various embodiments of the present subject matter.

FIG. 11 illustrates a system 1120 including a programmer 1122, an implantable neural stimulator (NS) device 1137 and an implantable cardiac rhythm management (CRM) device 1138, according to various embodiments of the present subject matter. Various aspects involve a method for communicating between an NS device 1137, such as an AHT device, and a CRM device 1138 or other cardiac stimulator. In various embodiments, this communication allows one of the devices 1137 or 1138 to deliver more appropriate therapy (i.e. more appropriate NS therapy or CRM therapy) based on data received from the other device. Some embodiments provide on-demand communications. In various embodiments, this communication allows each of the devices 1137 and 1138 to deliver more appropriate therapy (i.e. more appropriate NS therapy and CRM therapy) based on data received from the other device. The illustrated NS device 1137 and the CRM device 1138 are capable of wirelessly communicating with each other, and the programmer is capable of wirelessly communicating with at least one of the NS and the CRM devices 1137 and 1138. For example, various embodiments use telemetry coils to wirelessly communicate data and instructions to each other. In other embodiments, communication of data and/or energy is by ultrasonic means.

In some embodiments, the NS device 1137 stimulates the baroreflex to provide NS therapy. In some embodiments, the NS device 1137 further senses ANS activity directly or using surrogate parameters, such as respiration and blood pressure, indicative of ANS activity. The CRM device 1138 includes cardiac stimulation capabilities, such as pacing and defibrillating capabilities. In some embodiments, the CRM device provides pulsatile information. Rather than providing wireless communication between the NS and CRM devices 1137 and 1138, various embodiments provide a communication cable or wire, such as an intravenously-fed lead, for use to communicate between the NS device 1137 and the CRM device 1138.

Some NS device embodiments are able to be implanted in patients with existing CRM devices, such that the functionality of the NS device is enhanced by receiving physiological data that is acquired by the CRM device. The functionality of two or more implanted devices is enhanced by providing communication capabilities between or among the implanted devices. In various embodiments, the functionality is further enhanced by designing the devices to wirelessly communicate with each other.

According to various embodiments, for example, the NS device is equipped with a telemetry coil or ultrasonic transducer, allowing data to be exchanged between it and the CRM device, allowing the NS device to provide NS therapy based no pulsatile information such as pulse rate and pulse phase. Embodiments of the NS device modify therapy based on electrophysiological parameters such as heart rate, minute ventilation, atrial activation, ventricular activation, and cardiac events. In addition, the CRM device modifies therapy based on data received from the NS device, such as mean arterial pressure, systolic and diastolic pressure, and baroreflex stimulation rate.

Figure 12:
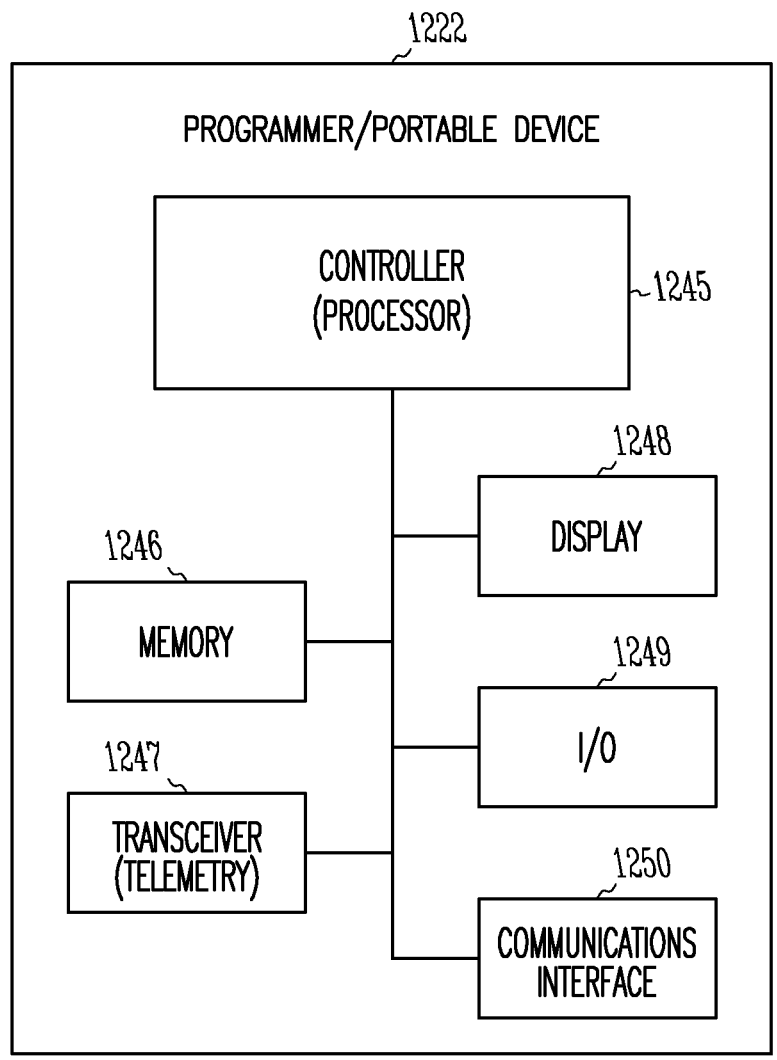
FIG. 12 illustrates a programmer such as illustrated in the systems of FIGS. 8 and 11 or other external device to communicate with the implantable medical device(s), according to various embodiments of the present subject matter.

FIG. 12 illustrates a programmer 1222, such as the programmer 822 and 1122 illustrated in the systems of FIGS. 8 and 11, or other external device to communicate with the implantable medical device(s) 1137 and/or 1138, according to various embodiments of the present subject matter. An example of another external device includes Personal Digital Assistants (PDAs) or personal laptop and desktop computers in an Advanced Patient Management (APM) system. The illustrated device 1222 includes controller circuitry 1245 and a memory 1246. The controller circuitry 1245 is capable of being implemented using hardware, software, and combinations of hardware and software. For example, according to various embodiments, the controller circuitry 1245 includes a processor to perform instructions embedded in the memory 1246 to perform a number of functions, including communicating data and/or programming instructions to the implantable devices. The illustrated device 1222 further includes a transceiver 1247 and associated circuitry for use to communicate with an implantable device. Various embodiments have wireless communication capabilities. For example, various embodiments of the transceiver 1247 and associated circuitry include a telemetry coil for use to wirelessly communicate with an implantable device. The illustrated device 1222 further includes a display 1248, input/output (I/O) devices 1249 such as a keyboard or mouse/pointer, and a communications interface 1250 for use to communicate with other devices, such as over a communication network.

The above-described functions of a system, whether implemented in two separate and distinct implantable devices or integrated as components into one implantable device, includes, but is not limited to, processes for performing NS therapy. One process involves sustaining baroreflex stimulation. The process can be performed by a processor executing computer-readable instructions embedded in memory, for example.

Figure 13:
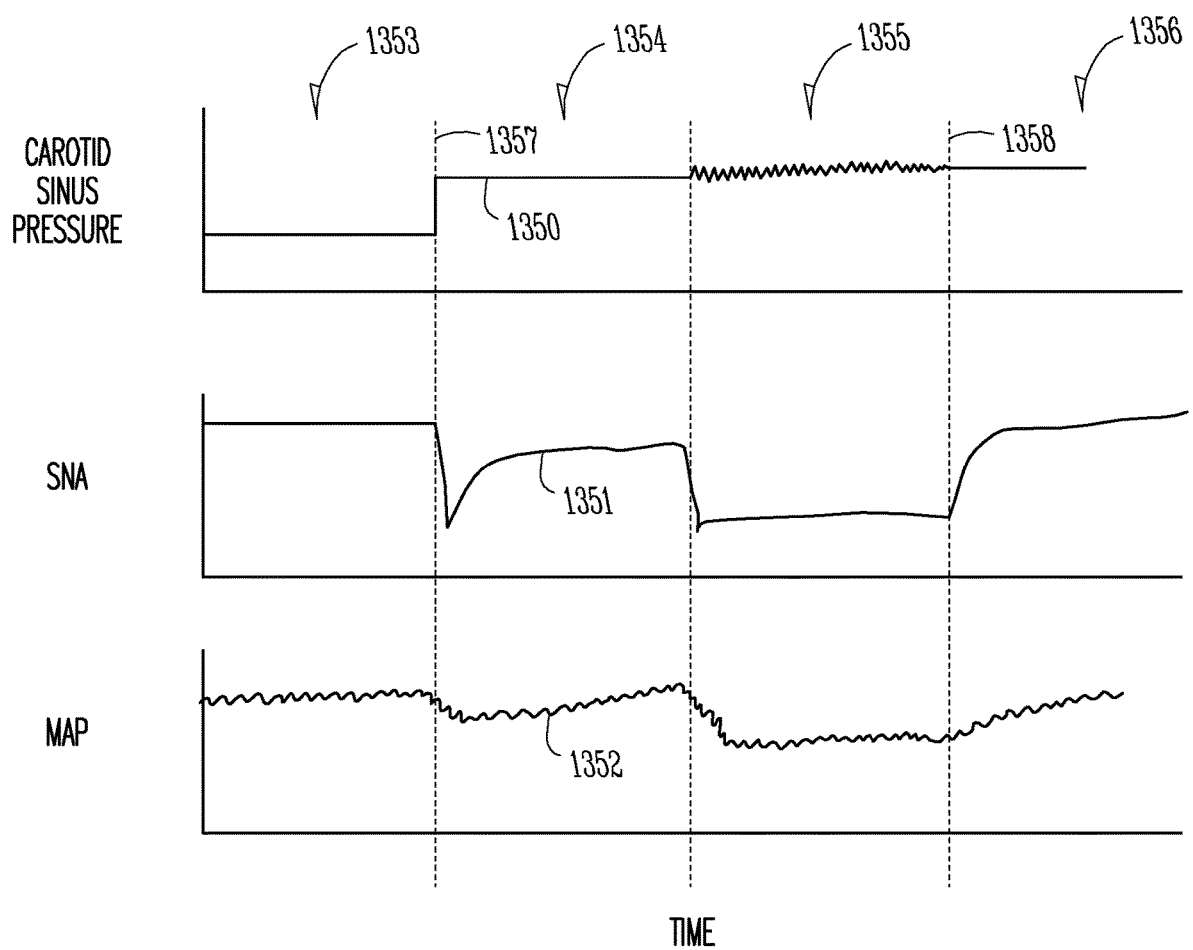
FIG. 13 illustrates baroreflex adaptation using a relationship between carotid sinus pressure, sympathetic nerve activity (SNA) and mean arterial pressure (MAP).

FIG. 13 illustrates baroreflex adaptation using a relationship between carotid sinus pressure 1350, sympathetic nerve activity (SNA) 1351 and mean arterial pressure (MAP) 1352. Internal pressure and stretching of the arterial wall, such as that which occurs at the carotid sinus, naturally activates the baroreflex and the baroreflex inhibits SNA. The carotid sinus pressure, the SNA and the MAP are illustrated for the following four time segments: (1) relatively low and constant carotid sinus pressure 1350 indicated at 1353; (2) relatively high and constant carotid sinus pressure 1350 indicated at 1354; (3) relatively high and pulsed carotid sinus pressure 1350 indicated at 1355; and (4) a return to a relatively high and constant carotid sinus pressure 1350 indicated at 1356.

When the carotid sinus pressure is relatively low and constant, as illustrated at 1353, the SNA is relatively high and constant, and the pulsating MAP is relatively high. When the carotid sinus pressure is increased to a relatively high and constant pressure at transition 1357, the SNA and MAP initially decrease due to the baroreflex and then increase due to the quick adaptation of the baroreflex to the increased carotid sinus pressure. However, when the carotid sinus pressure pulsates similar to naturally-occurring blood pressure pulses, as illustrated at 1355, the SNA and MAP decrease to relatively low levels and are maintained at these relatively low levels. When the carotid sinus pressure changes from a pulsed to constant pressure at transition 1358, the SNA and MAP both increase again due to the adaptation of the baroreflex. The present subject matter modulates the baroreflex stimulation to mimic the effects of the naturally-occurring pulse pressure and prevent baroreflex adaptation.

Figure 14:
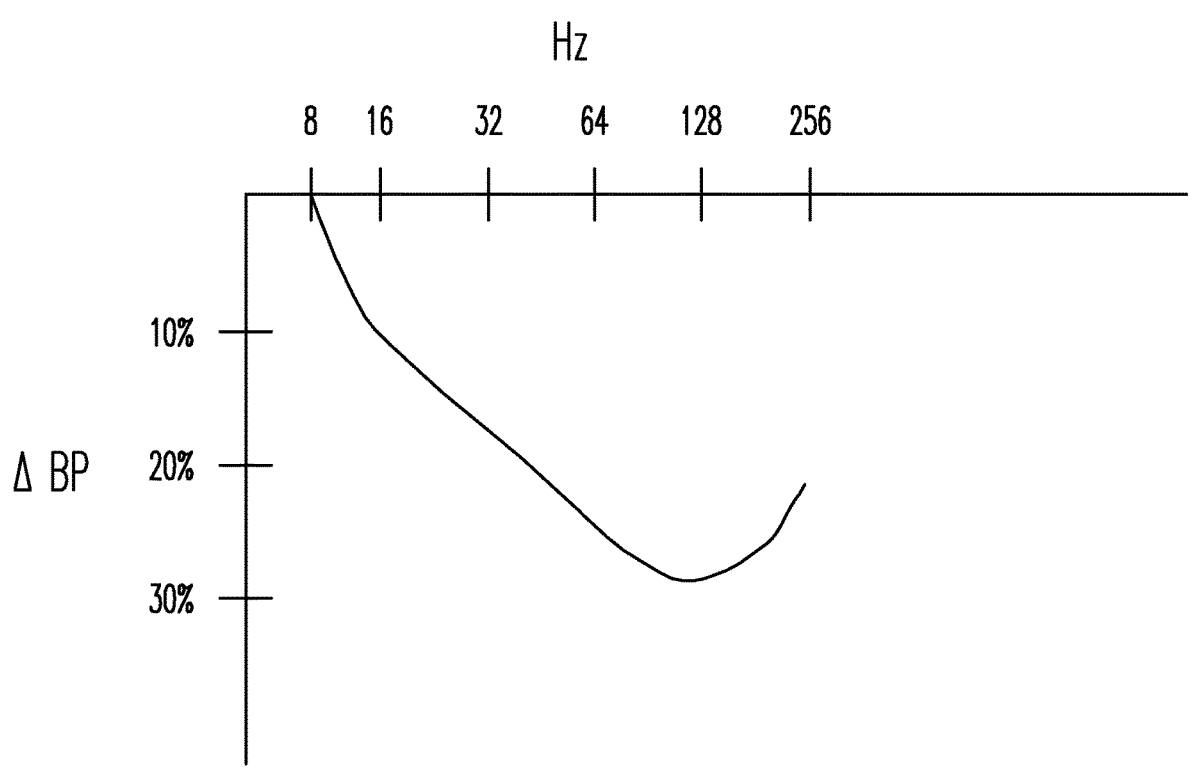
FIG. 14 is a graphical illustration of the relationship between a change in blood pressure and a rate of a stimulation signal.

FIG. 14 is a graphical illustration of the relationship between a change in blood pressure and a rate of a stimulation signal. The figure illustrates that the frequency of the stimulation signal significantly affects the decrease in blood pressure, which is a surrogate baroreflex parameter indicating the inhibition of SNA. The figure illustrates that a maximum decrease in blood pressure occurs at a stimulation frequency within a range from about 64 to about 256 Hz, and occurs approximately at 128 Hz.

Various embodiments of the present subject matter modulate the frequency of the stimulation signal to modulate the blood pressure to mimic the effects of a naturally-occurring pulse as generally illustrated at 1355 in FIG. 13. Various embodiments stimulate with a frequency between approximately 8 Hz and approximately 512 Hz, or various ranges within this range such as approximately 16 Hz to approximately 128 Hz, approximately 32 Hz to approximately 128 Hz, for example. Other embodiments modulate other parameters of the stimulation signal to mimic the effects of the naturally-occurring pulse, and thus prevent or reduce baroreflex adaptation. By preventing the baroreflex from adapting to increased baroreflex activity, long-term baroreflex stimulation can be used to achieve reflex reduction in hypertension. Varying the baroreflex stimulation maintains the reflex inhibition of SNA and abates (i.e. nullify or reduce in degree or intensity) adaptation to increased baroreflex activity that occurs during constant stimulation.

Figure 15:
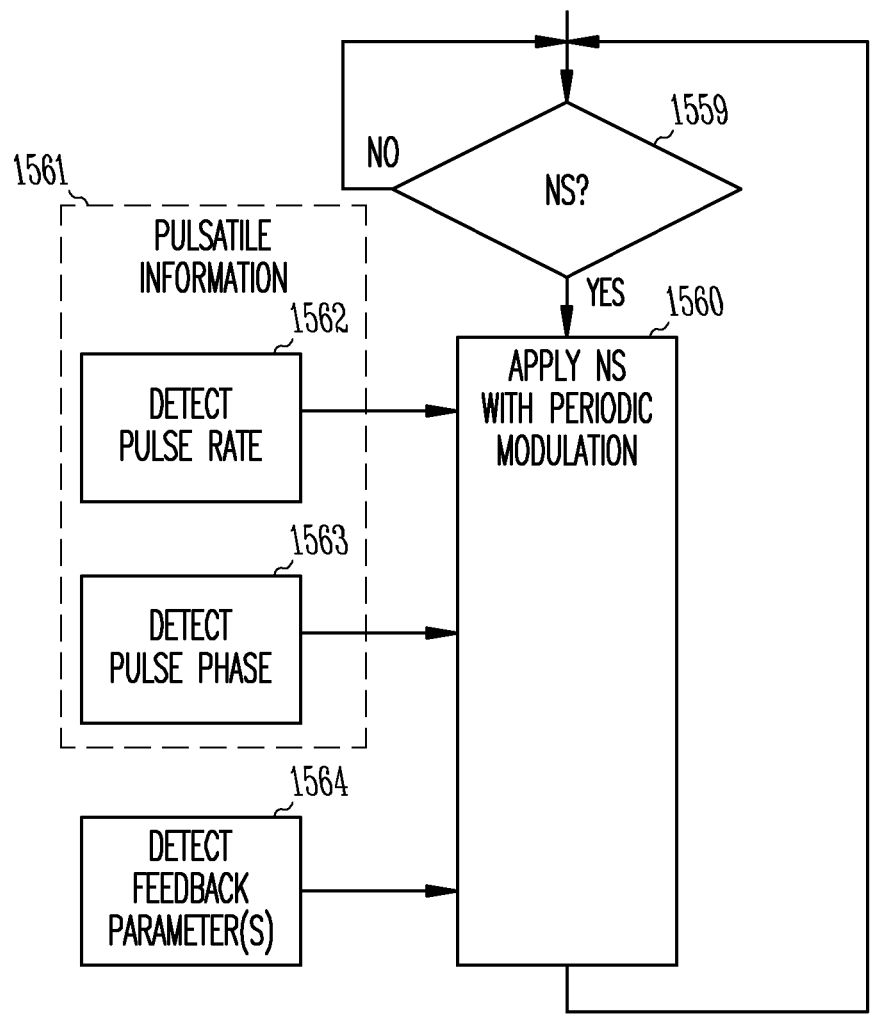
FIG. 15 illustrates a method to periodically modulate neural stimulation, according to various embodiments of the present subject matter.

FIG. 15 illustrates a method to periodically modulate neural stimulation, according to various embodiments of the present subject matter. At 1559, it is determined whether neural stimulation is to be provided. Upon determining that neural stimulation is to be provided, neural stimulation is applied with periodic modulation to mimic pulsatile pressure, as generally illustrated at 1560. In various embodiments, the periodic modulation, or other variation, of the neural stimulation signal is based on detected pulsatile information 1561 such as a detected pulse rate 1562 and/or a detected pulse phase 1563. Some embodiments further base the periodic modulation based on detected feedback parameters 1564, such as detected respiration, detected nerve traffic, detected blood pressure, and the like. These feedback parameters allow the stimulation to be tailored to achieve a desired effect.

Figure 16:
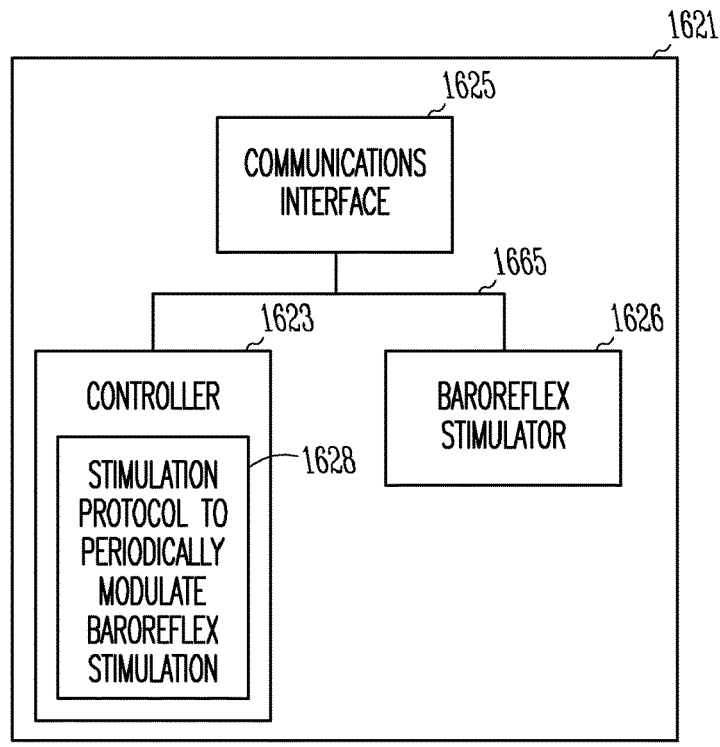
FIG. 16 illustrates a neural stimulation device, according to various embodiments of the present subject matter.

FIG. 16 illustrates a neural stimulation device, according to various embodiments of the present subject matter. The illustrated device 1621 includes a controller 1623, a baroreflex stimulator 1626 and a communications interface 1625 adapted to communicate with each other using bus 1665. The controller 1623 is adapted to implement a baroreflex stimulation protocol 1628 to periodically modulate the baroreflex stimulation provided by the stimulator 1626. The modulation is preprogrammed in various embodiments. In some embodiments, the modulation is based on detected parameters, such as detected pulsatile parameters. These detected parameters are capable of being detected by another device, such as a blood pressure monitor or implantable CRM device, and communicated to the device 1621 via the communications interface 1625.

Figure 17:
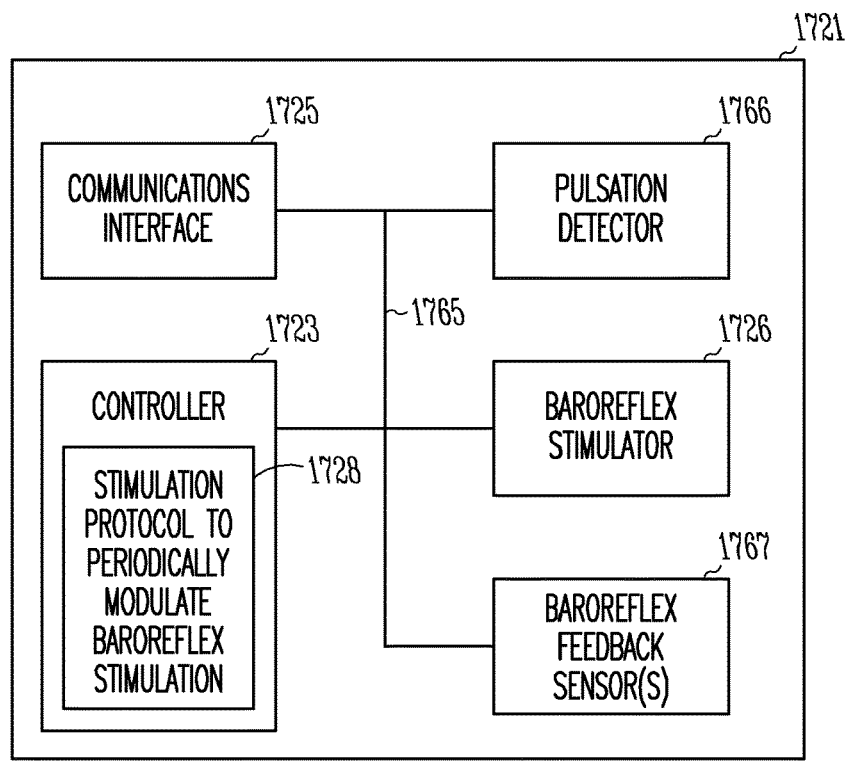
FIG. 17 illustrates an implantable neural stimulation (NS) device with sensing and/or detecting capabilities, according to various embodiments of the present subject matter.

FIG. 17 illustrates an implantable neural stimulation (NS) device with sensing and/or detecting capabilities, according to various embodiments of the present subject matter. The illustrated device 1721 includes a controller 1723, a baroreflex stimulator 1726, and a communications interface 1725 adapted to communicate with each other using bus 1765. The controller 1723 is adapted to implement a stimulation protocol 1728 to periodically modulate baroreflex stimulation. Some device embodiments include a pulsation detector 1766 to detect pulsatile information such as pulse rate and/or pulse phase, and to communicate using bus 1765. Some device embodiments include baroreflex feedback sensors 1767 to detect nerve activity and/or a surrogate parameter of nerve activity, and to communicate using bus 1765. Examples of a surrogate parameter of nerve activity include respiration and blood pressure.

Figure 18:
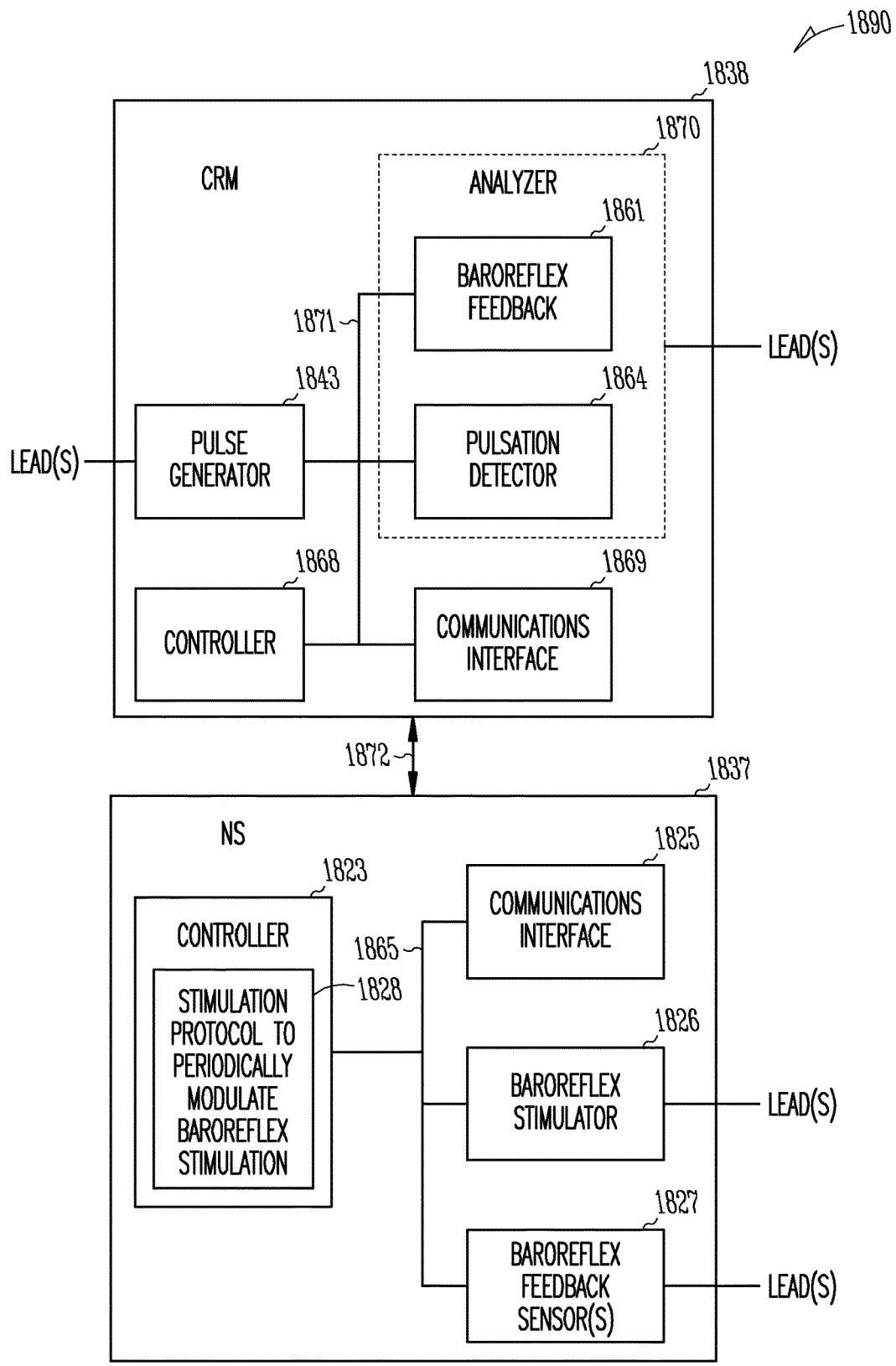
FIG. 18 illustrates a system including an implantable neural stimulation (NS) device and an implantable cardiac rhythm management (CRM) device, according to various embodiments of the present subject matter.

FIG. 18 illustrates a system 1890 including an implantable neural stimulation (NS) device 1837 and an implantable cardiac rhythm management (CRM) device 1838, according to various embodiments of the present subject matter. The CRM device 1838 includes a pulse generator 1843, a controller 1868, a communications interface 1869 and an analyzer 1870 to analyze sensed activity from at least one lead. Bus 1871 provides a means of communicating within the CRM device. The illustrated analyzer 1870 includes a pulsation detector 1864. Various embodiments of the analyzer 1870 further includes a baroreflex feedback module 1861 to detect parameters indicative of the baroreflex such as heart rate, respiration and the like.

The NS device 1837 includes a controller 1823, a communications interface 1825 and a baroreflex stimulator 1826 to stimulate a baroreceptor site or baroreflex pathway using at least one lead. Bus 1865 provides a means of communicating within the NS device. The controller 1823 implements a stimulation protocol 1828 to periodically modulate the baroreflex stimulation provided by the baroreflex stimulator 1828. Various embodiments of the NS device 1837 further include baroreflex feedback sensors 1867 to detect parameters indicative of the baroreflex such as nerve traffic, pulse rate and the like. These parameters provide feedback information to the controller 1823, enabling the controller to tailor the baroreflex stimulation to achieve desired physiologic results. The CRM device 1838 and the NS device 1837 are adapted to communicate with each other, as illustrated at 1872. According to various embodiments, the controller 1823 uses the protocol 1828 to modulate the baroreflex stimulation using parameters provided by the analyzer 1870 in the CRM device 1838.

Figure 19A:
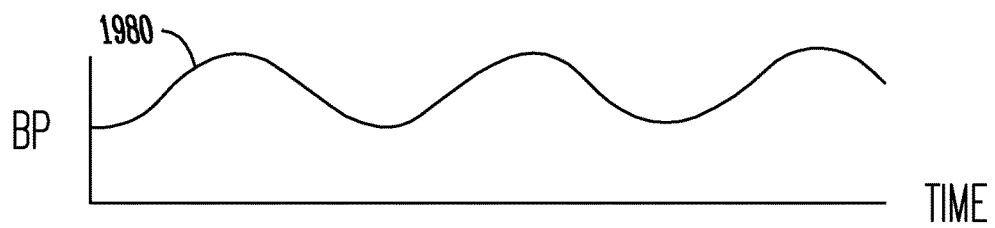
FIG. 19A illustrates a pulse and FIGS. 19B-19D illustrate various stimulation protocol embodiments to modulate a stimulation signal based on the pulse.
Figure 19B:
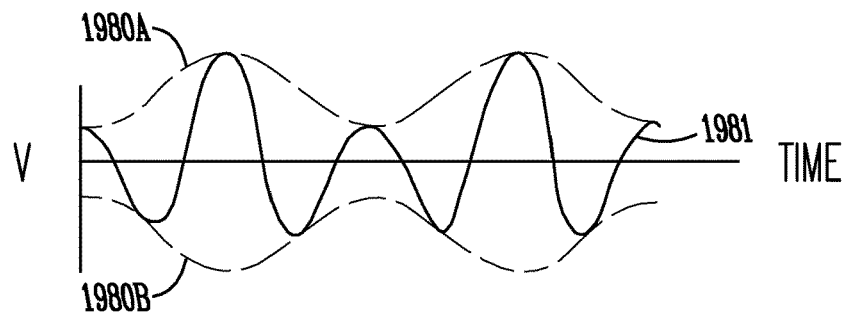
Figure 19C:
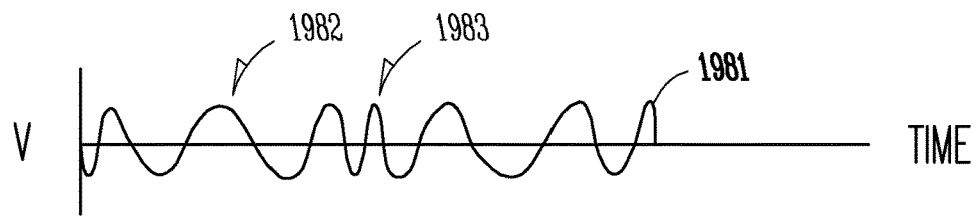
Figure 19D:
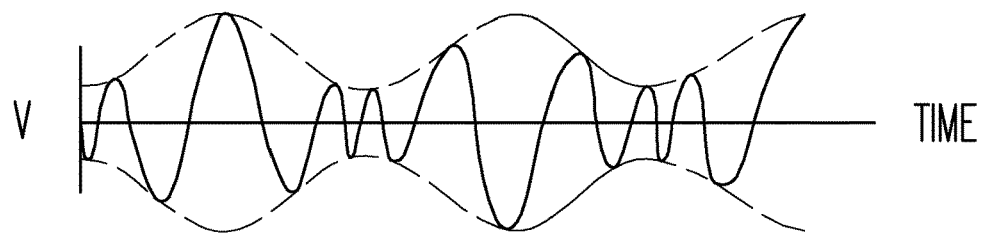

FIG. 19A illustrates a pulse 1980 and FIGS. 19B-19D illustrate various stimulation protocol embodiments to modulate a stimulation signal based on the pulse. A simple example of a resting pulse rate is about 60 beats per minute, which corresponds to 1 beat per second or 1 Hz. Some stimulation protocol embodiments closely correspond to the pulse. For example, some embodiments modulate the stimulation signal with a period of modulation approximately equal to the pulse period (e.g. on the order of approximately 1 Hz for resting pulse rate to approximately 2 Hz for exercise). In addition, some embodiments modulate the stimulation signal approximately in-phase with the pulse phase, such that more stimulation is provided at higher pulse pressure and less stimulation is provided at lower pulse pressure. However, the present subject matter is not limited to protocol embodiments that closely correlate the modulate stimulation signals to the rate and/or phase of the pulse. The effect of the pulsatile pressure on the baroreflex is capable of being obtained using other modulation protocols.

FIG. 19B illustrates amplitude modulation corresponding to the pulse signal. The illustrated dotted lines 1980A and 1980B generally correspond to the pulse rate and phase of the pulse 1980 in FIG. 19A, and provide an envelope for the amplitude modulation of the stimulation signal 1981. The phases of the illustrated stimulation signal 1981 and pulse 1980 are such that the timing for maximum amplitude of the stimulation signal generally corresponds to the maximum blood pressure for pulse 1980. Other embodiments do not attempt to align the phases of the pulse and stimulation signal. The stimulation signal 1981 is illustrated with a low frequency (illustrated with a frequency of approximately 2 Hz with respect to a 60 beats per minute pulse) for simplicity. Other frequencies can and are preferably used. For example, various embodiments provide a stimulation signal within a frequency range generally illustrated in FIG. 14 to increase the effectiveness of the signal in reducing the blood pressure. By using a more effective frequency for the stimulation signal, lower voltages can be used to stimulate the baroreflex. Lower voltages are generally desirable to reduce inflammation from stimulation and to prevent unintended capture of cardiac tissue, for example. The amplitude of the signal depends on the placement of the electrodes and the tissue. Various embodiments provide stimulation signals with an amplitude on the order of approximately 100 µA to 10 mA.

FIG. 19C illustrates frequency modulation corresponding to the pulse signal. With reference to FIG. 14, the effectiveness of a stimulation signal in inducing the baroreflex is dependent on the frequency. Thus, various embodiments of the present subject matter vary the frequency of the stimulation signal 1981 between more effective and less effective frequencies. The frequency for the illustrated stimulation signal 1981 is varied using a modulation period corresponding to the period of the pulse. However, the present subject matter is not so limited, as other modulation periods are capable of effectively mimicking the pulsatile effect.

The stimulation signal is illustrated with a low frequency for simplicity. Other frequencies can and are preferably used. For example, various embodiments provide a stimulation signal within a frequency range generally illustrated in FIG. 14 to increase the effectiveness of the signal in reducing the blood pressure.

For example, the maximum effectiveness corresponds to a frequency within a range of 32 Hz and 256 Hz.

The following examples assume a stimulation signal having a frequency of approximately 128 Hz is relatively more effective at inducing a baroreflex, and that frequencies that are either higher or lower than 128 Hz are relatively less effective at inducing a baroreflex. The slowest frequencies 1982 in the stimulation signal 1981 are illustrated at the time of the highest blood pressure in the pulse 1980, and the highest frequencies 1983 are illustrated at the time of the lowest blood pressure in the pulse 1980. Thus, the frequency of the illustrated stimulation signal is modulated from approximately 128 Hz at a time corresponding to the highest blood pressure to a larger frequency (256 Hz or larger) at a time corresponding to the lowest blood pressure. In other embodiments, which are not illustrated in the figures, the highest frequencies in the stimulation signal are provided at the time of the highest blood pressure in the pulse, and the lowest frequencies are provided at the time of the lowest blood pressure in the pulse. In such embodiments, for example, the frequency of the stimulation signal is modulated from 128 Hz at a time corresponding to the highest blood pressure to a lower frequency (approximately 8 to 64 Hz) at a time corresponding to the lowest blood pressure. Other embodiments, which are not illustrated in the figures, sweep between a relatively low frequency (e.g. 8 Hz) to a relatively high frequency (e.g. 256 Hz), and time the frequency shift such that the stimulation signal has a frequency of 128 Hz at a time that corresponds to the largest blood pressure in the pulse. Various frequency modulation embodiments closely correspond to the pulse rate, various frequency modulation embodiments closely correspond to both the pulse rate and pulse phase, and various frequency modulation embodiments do not closely correspond to either the pulse rate or pulse phase but still are capable of mimicking the pulsatile effect.

FIG. 19D illustrates a stimulation protocol that includes both amplitude modulation and frequency modulation. Again, as provided above, the stimulation signal is illustrated with a low frequency for simplicity, and other frequencies can and are preferably used. The amplitude modulation and frequency modulation were discussed above. For the sake of brevity, the discussion will not be repeated here. FIG. 19D illustrates that more than one parameter of the stimulation protocol can be modulated to modulate the stimulation of the baroreflex.

FIG. 20A illustrates a pulse 2080 and FIG. 20B illustrates an example of a burst frequency modulation protocol to mimic effects of pulsatile pressure. The intervals between duty cycles 2084 are varied between shorter and larger intervals over the course of a modulation period for the duty cycles. The illustration shows about fourteen pulse cycles for every duty cycle modulation period, and further illustrates a stimulation frequency within each burst (or duty cycle) of approximately 2 Hz with respect to a 1 Hz (60 beats per minute pulse). Again, as provided above, the stimulation signal is illustrated with a low frequency for simplicity, and other frequencies can and are preferably used. In various embodiments, the frequency of the signal within each burst is within a range approximately 8 Hz to approximately 256.

According to various embodiments the duty cycle modulation period corresponds to the pulse period. A train of duty cycles are provided during a pulse period on the order of 1 second for a resting heart rate, and the intervals between duty cycles are modulated between shorter and larger intervals during the pulse period. According to various embodiments, the duty cycle modulation period is larger than the pulse period, as generally illustrated in FIGS. 20A and 20B. A train of duty cycles are provided and duty cycle intervals are modulated between shorter and larger intervals over the course of a plurality of pulse periods. With reference to FIG. 6, various embodiments maintain a maximum interval between duty cycles to be under 60 seconds (e.g. 30 seconds) to be sufficient to maintain a desired blood pressure response.

Various embodiments combine the duty cycle modulation protocol with an amplitude modulation protocol, various embodiments combine the duty cycle modulation protocol with a frequency modulation protocol, and various embodiments combine the duty cycle modulation protocol with both the amplitude modulation protocol and the frequency modulation protocol.

The illustrations in FIGS. 19A-D and 20A-B include sinusoidal waveforms. Various embodiments use other waveforms such as square waveforms, triangular waveforms, and the like. Thus, the subject matter of the present application is not limited to sinusoidal waveforms or any other particular waveform.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

References to modulation and periodic modulation are provided as examples of protocols to abate (nullify or reduce in degree or intensity) baroreflex adaptation. Other protocols to vary baroreflex stimulation can be used to abate baroreflex adaptation.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. For example, various embodiments combine two or more of the illustrated processes. Two or more sensed parameters can be combined into a composite parameter used to provide a desired neural stimulation (NS) or anti-hypertension (AHT) therapy. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A system for delivering a neurostimulation therapy, comprising:
   a neurostimulation generator configured to generate a pre-programmed neurostimulation waveform with pre-programmed modulation, wherein the pre-programmed neurostimulation waveform with pre-programmed modulation includes a periodically-modulated pulse train in which a train of pulses in an electrical signal used to deliver neurostimulation is modulated at a modulation frequency over a plurality of modulation periods that repeatedly occur at regular intervals; and
   a controller operably connected to the neurostimulation generator to deliver the neurostimulation therapy by generating the pre-programmed neurostimulation waveform with the pre-preprogrammed modulation using pre-programmed instructions to generate the periodically-modulated pulse train from the neurostimulation, wherein the periodically-modulated pulse train is defined by the pre-programmed instructions and includes at least one parameter modulated over a plurality of values during each of the plurality of modulation periods to provide the pre-programmed modulation.

2. The system of claim 1, wherein the at least one parameter includes a pulse amplitude.

3. The system of claim 1, wherein the at least one parameter includes a pulse frequency.

4. The system of claim 1, wherein the at least one parameter includes both a modulated pulse amplitude and a modulated pulse frequency.

5. The system of claim 1, wherein the at least one parameter includes a modulated burst frequency.

6. The system of claim 1, wherein the at least one parameter includes a modulated morphology.

7. The system of claim 1, wherein the neurostimulation therapy includes an autonomic neurostimulation therapy.

8. The system of claim 1, further comprising at least one feedback sensor configured for use in sensing a physiologic parameter, and using the sensed physiologic parameter as feedback to control the neurostimulation therapy, wherein the pre-programmed modulation of the pre-programmed neurostimulation waveform is not based on the sensed physiologic parameter.

9. The system of claim 8, wherein the at least feedback sensor includes a nerve traffic sensor.

10. A method for operating a neurostimulation system having a neurostimulation generator, a controller, a memory with a pre-programmed instructions to generate a pre-programmed neurostimulation waveform with pre-programmed modulation, wherein the pre-programed neurostimulation waveform with pre-programmed modulation includes a periodically-modulated pulse train in which a train of pulses in an electrical signal used to deliver neurostimulation is modulated at a modulation frequency over a plurality of modulation periods that repeatedly occur at regular intervals, the method comprising:
    using the controller and the neurostimulation generator to deliver the neurostimulation therapy by implementing the pre-programmed instructions to generate the pre-programmed neurostimulation waveform with the pre-preprogrammed modulation, including the periodically-modulated pulse train defined by the pre-programmed instructions, wherein the periodically-modulated pulse train includes at least one parameter modulated over a plurality of values during each of the plurality of modulation periods to provide the pre-programmed modulation.

11. The method of claim 10, wherein the at least one parameter includes a modulated burst frequency.

12. The method of claim 10, wherein the at least one parameter includes at least one of a modulated pulse amplitude or a modulated pulse frequency.

13. The method of claim 10, wherein the at least one parameter includes a modulated burst frequency.

14. The method of claim 10, wherein the at least one parameter includes a modulated morphology.

15. The method of claim 10, further comprising using sensed nerve traffic as feedback to control the neurostimulation therapy.

16. A non-transitory machine-readable medium including instructions, which when executed by a controller of a neuromodulation system that also includes a neurostimulation generator, a memory and a programmed therapy application with a pre-programmed instructions in the memory to generate a pre-programmed neurostimulation waveform with pre-programmed modulation, cause the controller to:

deliver a neurostimulation therapy by generating the pre-programmed neurostimulation waveform with the pre-preprogrammed modulation, including the periodically-modulated pulse train, wherein the periodically-modulated pulse train includes at least one parameter modulated over a plurality of values during each of a plurality of modulation periods to provide the pre-programmed modulation, wherein the pre-programmed neurostimulation waveform with the pre-programmed modulation includes a periodically-modulated pulse train in which a train of pulses in an electrical signal used to deliver neurostimulation is modulated at a modulation frequency over the plurality of modulation periods that repeatedly occur at regular intervals.

17. The non-transitory machine-readable medium of claim 16, wherein the at least one parameter includes a modulated morphology.

18. The non-transitory machine-readable medium of claim 16, wherein the at least one parameter includes at least one of a modulated pulse amplitude or a modulated pulse frequency.

19. The non-transitory machine-readable medium of claim 16, wherein the at least one parameter includes a modulated burst frequency.

20. The non-transitory machine-readable medium of claim 16, wherein the at least one parameter includes both a modulated pulse amplitude and a modulated pulse frequency.

* * * * *